United States Patent
Demirel et al.

(10) Patent No.: US 9,663,658 B2
(45) Date of Patent: *May 30, 2017

(54) COMPOSITIONS AND METHODS RELATED TO PROTEINS CAPABLE OF REVERSIBLE TRANSITION TO A MELT

(71) Applicant: The Penn State Research Foundation, University Park, PA (US)

(72) Inventors: Melik Demirel, State College, PA (US); Abdon Pena-Francesch, State College, PA (US)

(73) Assignee: The Penn State Research Foundation, Univeristy Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/774,410

(22) PCT Filed: Mar. 13, 2014

(86) PCT No.: PCT/US2014/025887
§ 371 (c)(1),
(2) Date: Sep. 10, 2015

(87) PCT Pub. No.: WO2014/160131
PCT Pub. Date: Oct. 2, 2014

(65) Prior Publication Data
US 2016/0024305 A1    Jan. 28, 2016

Related U.S. Application Data

(60) Provisional application No. 61/920,449, filed on Dec. 23, 2013, provisional application No. 61/782,722, filed on Mar. 14, 2013.

(51) Int. Cl.
| | |
|---|---|
| *A61K 35/618* | (2015.01) |
| *C08L 89/00* | (2006.01) |
| *C09J 189/00* | (2006.01) |
| *C08L 3/02* | (2006.01) |
| *C07K 14/435* | (2006.01) |
| *C08J 3/03* | (2006.01) |
| *C08J 3/09* | (2006.01) |
| *C08J 3/18* | (2006.01) |
| *C08K 5/00* | (2006.01) |
| *C09J 5/00* | (2006.01) |
| *A61K 38/00* | (2006.01) |

(52) U.S. Cl.
CPC ........ *C08L 89/00* (2013.01); *C07K 14/43504* (2013.01); *C08J 3/03* (2013.01); *C08J 3/09* (2013.01); *C08J 3/18* (2013.01); *C08K 5/0016* (2013.01); *C08L 3/02* (2013.01); *C09J 5/00* (2013.01); *C09J 189/00* (2013.01); *C08J 2389/00* (2013.01); *C08L 2201/54* (2013.01); *C08L 2203/12* (2013.01); *C08L 2203/16* (2013.01); *C09J 2489/00* (2013.01)

(58) Field of Classification Search
None
See application file for complete search history.

(56) References Cited

U.S. PATENT DOCUMENTS

| | | | |
|---|---|---|---|
| 5,679,171 A * | 10/1997 | Saga | ................. H01L 21/02052 134/2 |
| 6,090,915 A | 7/2000 | Herreid | |
| 7,303,646 B2 | 12/2007 | Qvist | |
| 2015/0068661 A1 * | 3/2015 | Mahdi | .................... C09J 175/08 156/71 |

FOREIGN PATENT DOCUMENTS

| | | |
|---|---|---|
| WO | 2006020594 | 2/2006 |
| WO | 2011149907 | 12/2011 |
| WO | 2013078557 | 6/2013 |
| WO | 2014/062134 A1 | 4/2014 |

OTHER PUBLICATIONS

Miserez et al., Sucker Rings from the Humboldt Squid Dosidicus gigas: The Role of Nanotubule Architecture on the Mechanical Properties, Mater. Res. Soc. Symp. Proc. vol. 1187. Jan. 1, 2009.
Miserez et al., Microstructural and Biochemical Characterization of the Nanoporous Sucker Rings from Dosidicus gigas, Adv. Mater. 2009, 21, 401-406. Jan. 1, 2009.
Staverman, Thermodynamic Aspects of the Glass-Rubber Transition, From the Centraal Laboratorium TNO, Delft (Netherlands). Jul. 19, 1966.

* cited by examiner

*Primary Examiner* — Anand Desai
*Assistant Examiner* — Samuel Liu
(74) *Attorney, Agent, or Firm* — Hodgson Russ LLP

(57) ABSTRACT

Provided are compositions and methods for making a variety of products. The methods involve mixing sucker ring teeth (SRT) protein and a plasticizer or a solvent to obtain a mixture of the SRT protein and the plasticizer. When the SRT is mixed with a plasticizer it is heated to between 32° C. and 195° C. to obtain an SRT protein melt. The melt is used to form a wide variety of products. When the SRT is mixed with a solvent, such as an organic solvent or an aqueous solvent, a solution of the SRT protein is formed, and is subsequently used to forming a product from the solution, wherein the product contains SRT protein.

11 Claims, 10 Drawing Sheets

Figure 2.

Protein sequences of ~50kDa for *Loligo Pealei* and *Loligo Vulgaris*

| *Loligo Vulgaris* |
|---|
| MGAMQLAVALIVLGISSSANGIFNGSTAGLGSQPSPYIGRSVSTVSHGSHYPAYGGWGYNLGSWGHG LGGLGSYGLHYPMSSSVSHVSHTAHSPLGYYGWGGYGQQSPLTHVSRTALPPVGWAFGGLYRGHG AQVSQSPVRYHGYSFGRPAVATRRVLYPKPVVSHVTHTIPHSGWGMGGFGGYVSSYPTGASVNTVSH GISHAPVYGGWGAGHAISTVAHGIHPTVTYGGMGLGGLYGGYGAHYPASTSVSHTTHSVPHTVGLG LGSLHGGWGGYGIGYGVHSPVGASVSTVSHGIGHPVGYGTWGLGSGAHYPVGQSVSTVSHGVHAPV VHGGLGLSGSSVSTVSHGVPSLGAYGGYGLGGLIGGHSVYHPTGSSISTVSHGVPSLGAYGGYGLGG LIGGHSVYHPTGSSISTVSHGVPSLGAYGGYGLGGLIGGHSVYHPTGSSISTVSHGVPSLGAYGGYGL GGIVGGYGAYNPTGSSISTVSHGVHSPVGYGGYGLGGLIGGYGAYHPAGSSISTVSHGINSLGAYGGY GNGGLLGGYGVPLPLSTTSHHTVTH (SEQ ID NO:1) |
| *Loligo Pealei* |
| MGAMQLAVALIVLGISSSANAVFNGSWVGLGSQPSPLIGKSVSTVSHGYHYPGYGGWGYGLGGWGH GLGGLGSYGLHYPMSSSVSHVSHTAHAPLGFSGWGGYAQHSPLTHVSRTALPPVGWAFGGIYRGHG AQVSQSPVRYHGYSLGHPSVATRRVVYPKPAVSHVTHTIPHADYGVSGLGGYVSSYPTGASINTVSHG ISHAPVYGGWGVGFPAGQAMSTVAHGIHPTVPYGGIGLGGLYGGYGAHFPAATSVSHTTHSVPHSV GWGLGGWGGYGLGYGVHAPVGASVSTVSHGVHAPVIHGGATLSTVSHGVPALGAYGGYGFGGIVG GHSVYHPTGTSVSTVSHGVPALGGYGLYGLGGIVGGHSVSTVSHGAPALGAYGGYGLGGLVGGFGA YHPAGSSISTVSHGVHAPVGFGGYGLGGYGLGGYGLGGYGLGGYGLGGVVGGFGGYHPVGSSVST VSHGAFGGHGLLGGYGVPLPLSTTSHHTVTH (SEQ ID NO:2) |

COMPOSITIONS AND METHODS RELATED TO PROTEINS CAPABLE OF REVERSIBLE TRANSITION TO A MELT

CROSS REFERENCE TO RELATED APPLICATIONS

This application claims priority to U.S. application No. 61/782,722, filed Mar. 14, 2013, and to U.S. application No. 61/920,449, filed Dec. 23, 2013, the disclosures of each of which are incorporated herein by reference.

STATEMENT REGARDING FEDERALLY SPONSORED RESEARCH

This invention was made with government support under Grant No. HL112114, awarded by the National Institutes of Health and Contract No. N00014-13-1-0595, awarded by the Office of Naval Research. The Government has certain rights in the invention.

FIELD OF THE INVENTION

The present disclosure relates generally to novel compositions comprising proteins which are capable of reversible transition, proteins that are provided as a melt, methods of making the compositions, methods of using the compositions, and articles of manufacture comprising the compositions.

BACKGROUND OF THE INVENTION

There has been a growing interest to create eco-friendly materials from synthetic and biological materials exhibiting multifunctional characteristics. Ideally, these materials would be engineered using renewable resources and processing strategies that reflect the "green" chemistry of biological systems. There have been many previous attempts to develop biomimetic materials from naturally occurring products, such that the products retain desirable functional and physical properties that would permit their usage across broad product groups. However, there are relatively few successes. There is accordingly an ongoing and unmet need to develop novel materials that can be produced easily from renewable resources, and which would offer a broad array of useful applications. The present invention meets these and other needs.

SUMMARY

The present disclosure relates to compositions and methods involving proteins which are modified such that they are markedly different from the proteins as they occur naturally. In particular, the disclosure involves manipulation of an anatomical feature referred to in the art as Squid Ring Teeth (SRT). We have discovered that the SRTs have micromechanical properties matching those of strong synthetic polymers. We have also unexpectedly discovered that these and other useful properties of native SRTs are preserved after transition to a melt or are mixed with a solvent and subsequently used to form an amorphous object, and that this is a fully reversible process. Accordingly, in various embodiments, the disclosure includes a processed, recyclable bioelastomer that has multifunctional properties, including but not necessarily limited to elastic and viscoelastic thermo-reversible behavior.

In one aspect the disclosure includes a method of making an amorphous product. The method comprises mixing SRT protein and a plasticizer to obtain a mixture of the SRT protein and the plasticizer. The mixture is heated to between 32° C. and 195° C. to obtain an SRT protein melt. The amorphous product is formed from the SRT protein melt, and the formation of the product is reversible. Thus, the product is recyclable and can be melted and reformed into the same or a different product(s). In non-limiting embodiments, forming the product comprises extruding the SRT protein melt, coating the SRT protein melt onto a surface, molding the SRT protein melt, or a combination thereof. In one embodiment, forming the product comprises cooling the SRT protein melt to form at least one structure having a three dimensional shape.

In various approaches, forming the product comprises forming an adhesive and/or cohesive layer. Such layers can be formed between two or more surfaces, and between two or more objects. In embodiments, forming the product comprises forming a film, fiber, ribbon or tube. In another aspect the disclosure includes compositions comprising SRT protein and a plasticizer, wherein the SRT protein is in the form of a melt and is at a temperature of between 32° C. and 195° C.

In another approach the disclosure includes a method of making a product comprising mixing SRT protein and an organic solvent or an aqueous solvent such that a solution of the SRT protein is formed, and subsequently forming a product from the solution, wherein the product comprises the SRT protein. This approach is fully reversible.

In yet another approach, a method is provided for adhering a first surface to a second surface. This comprises contacting the first surface with a composition comprising SRT protein and an aqueous plasticizer, wherein the composition is between 32° C. and 195° C. on the first surface, contacting the composition on the first surface with the second surface, and cooling the composition to a temperature below 32° C. such that the composition adheres the first surface to the second surface. The composition can be both adhesive and cohesive. This process is suitable for adhering and maintaining adherence of products to one another in underwater and other environments.

In another embodiment, the disclosure includes products formed by performing any of the methods disclosed herein. Thus, the disclosure includes one or more an artificially shaped amorphous articles which comprise or consist of SRT protein.

DESCRIPTION OF THE FIGURES

FIG. 2. Amino acid sequences of ~50 kDa for *Loligo Pealei* (SEQ ID NO:2) and *Loligo Vulgaris* (SEQ ID NO:1).

Diverse SRT processing methods (electrospining, film formation by solvent evaporation, ultrasonification of protein melt and nanowetting) are used in the production of fibers, thin films, colloids and nanotubes.

Figure 10:
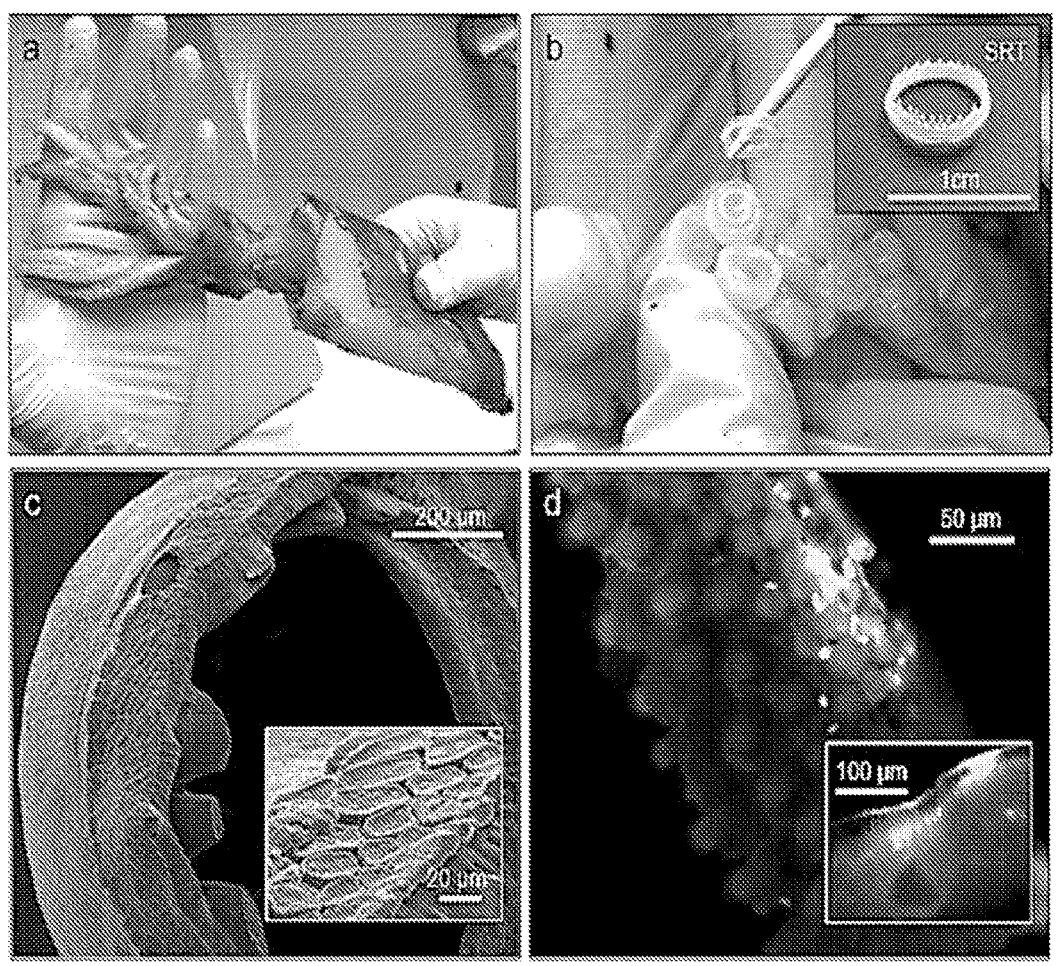

FIG. 10. Capture of European squid and extraction of SRT and its electron microscope image with the surrounding tissue analyzed by fluorescent labeling.

Figure 11:
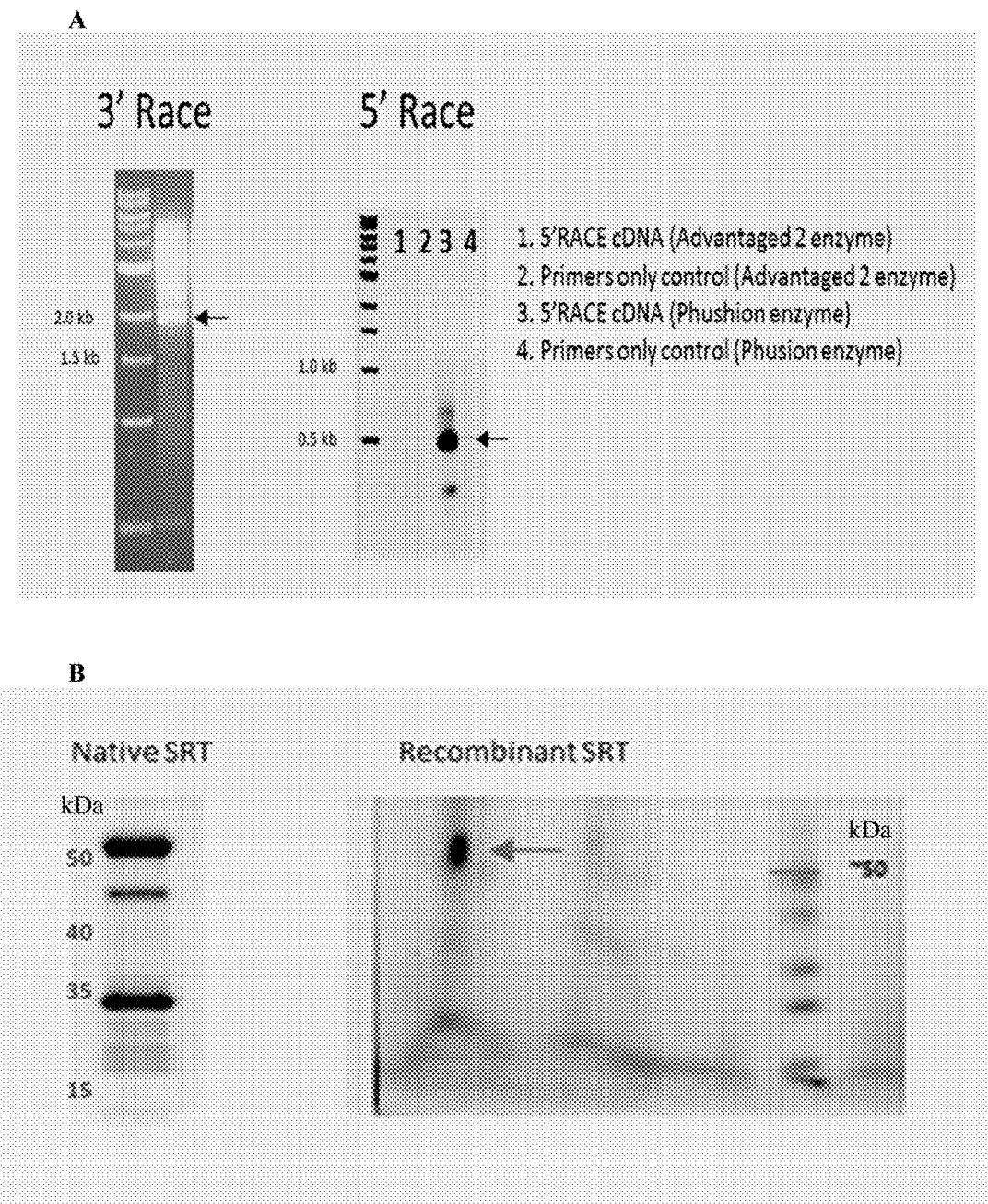

FIG. 11. A. RACE products made in determining the *Loligo Vulgaris*-SRT-50 amino acid sequence. This technique permitted identifying the cDNA that encodes the open reading frame for the *Loligo Vulgaris*-SRT-50 amino acid sequence. B. Photographic representation of recombinantly expressed SRT analyzed via SDS-PAGE separation.

DETAILED DESCRIPTION OF THE INVENTION

The present disclosure relates to compositions and methods involving proteins which are modified such that they are markedly different from the proteins as they occur naturally.

The disclosure generally involves manipulations of material that is present in an anatomical feature characteristic of a number of particular types of cephalopods, namely, the squids. The anatomical feature is referred to in the art as Squid Ring Teeth (SRT). Those familiar with squid anatomy will understand the meaning of the term Sucker Ring Teeth and SRT. SRT are grappling-hook-like structures lining the tentacles used for predatory attacks (FIG. 10). The protein-based SRTs exhibit a precise nanotubular architecture (FIG. 10) and feature micro-mechanical properties matching those of strong synthetic polymers, with elastic moduli in the range of 1-10 GPa. Remarkably, these robust properties are achieved in the absence of covalent bonds between the constituent proteins, which are soluble in weak acidic conditions, implying that the cooperation of weak interactions is responsible for holding the entire structure together into a robust supramolecular network that has properties further disclosed herein. In particular, we have now determined that useful properties of the SRT are preserved after transition to a melt or are mixed with a solvent. We have further discovered that transition of the SRT to a melt is fully reversible. The invention thus provides a novel form of SRT, methods which take advantage of it, articles of manufacture formed from SRT melts and solutions, and methods of making such articles formed from SRT melts and SRT solutions. The invention also provides a recyclable bioelastomer that has multifunctional properties, including but not necessarily limited to elastic and viscoelastic thermo-reversible behavior.

In one aspect of the disclosure, SRT proteins are subjected to a processing step so that they undergo transition to a melt. A "melt" as the term is used herein does not refer to a phase transition, i.e., from solid to liquid. A "melt" instead refers to a glass transition, which is not a physical thermodynamic phase transition. The glass transition is the change from one condensed state (glass) to another condensed state (melt). The melt is achieved at least in part by subjecting the SRT protein to a heat treatment which facilitates the glass transition. The glass transition does not occur in nature and imparts to the compositions markedly different properties from the proteins as they occur in nature, which include but are not necessarily limited to the capability to use the melt form for molding, such as by injection molding, thermoforming, thermoform extrusion, shaping, re-shaping, forming a fiber or wire, a thread, and/or forming a nano-structure, such as a nano-pillar, and/or forming a film. Likewise, products formed from an SRT melt are markedly different from SRT proteins as they are found in nature.

Forming a melt is achieved by heating SRT protein to a temperature between 32±4° C. in and 118±4° C. This range, as well as all ranges disclosed herein, is inclusive of the upper and lower limits, and includes each digit there between, and all ranges within those limits. Thus, in embodiments, forming a melt involves subjecting SRT protein to a temperature between 28° C. and 195° C. The melt is generally formed in the presence of a plasticizer. Suitable plasticizer include, but are not limited to, water, glycerol, 1,4-Butanediol, Dibutyl tartrate, Dibutyl phthalate, Lactic acid, Octanoic acid, Plamitic acid, Sorbitol, Sucrose, and diacetyl tartaric acid ester of monodiglycerides (DATEM).

In an aqueous plasticizer, such as deionized or purified water, the glass transition temperature is 32±4° C. In a plasticizer that is, for example, a sugar alcohol such as glycerol, the glass temperature is higher, such as 118±4° C. A component of this disclosure is related to our discovery that when heated above 195° C., the protein melt denatures or oxidizes.

In various embodiments we demonstrate that heating of SRT to form a melt (but not above the 195° C. denaturation point) when the SRT is mixed with a plasticizer, the melt flows like a viscoelastic liquid and can be molded and extruded. In connection with this we show, among other properties, that the protein melt has a peculiar underwater adhesive response, although the native (i.e., prior to processing) SRT is not adhesive in water. Thus, the disclosure provides in various embodiments compositions and methods for use of processed SRT in underwater or other predominantly or partially aqueous environments. As will be described more fully below, the disclosure includes combining the proteins with wetting materials, asymmetric transport materials, asymmetric friction materials, plasticizers, polysaccharides, carbohydrates, sugar alcohols, and other components.

In another aspect, the disclosure includes mixing SRT protein with a solvent without the need for a heat treatment. This aspect involves mixing SRT protein with an organic solvent, or an aqueous solvent. In this regard, SRT protein can be dissolved in some organics (e.g., hexafluoro-2-propanol (HFIP)) and acidic or alkaline media. The protein structure of SRT is held together by weak forces (hydrogen bonding), and breaking these inter-domain hydrogen bonds can dissolve it. However, the protein can be recovered if the solvent is evaporated or solution is titrated to SRTs isoelectric point (i.e., pH=6.7). Therefore, in embodiments, the SRT can be deposited as a thin film on surfaces via evaporation or titration. In embodiments, a thin film is a layer of material ranging from fractions of a nanometer (i.e., a monolayer) to several micrometers in thickness. Thus, the thin film can range from 0.1 nanometer, to 5 µm in thickness, including all ranges and integers to the first decimal point there between. Additionally, SRT colloids can be created by ultrasonication from bulk phase or by surfactant induced aggregation from solution phase. In embodiments the aqueous solvent contains at least 51% water. In embodiments, the organic solvent is a fluorinated solvent. Other solvents include DMSO, weak acids such as formic acid and acetic acids, or diluted strong acids such as hydrochloric acid (~pH=3), and weak bases such as ammonia or diluted strong bases such as diluted sodium hydroxide (pH=11), In general, mixing the SRT with a solvent comprises adding an organic solvent or an aqueous solvent to SRT protein such that a solution of the SRT protein is formed, and subsequently forming a product from the solution, wherein the product comprises the SRT protein. In embodiments, this approach can involve removing at least some of the solvent from the solution to form the product.

In embodiments the disclosure includes compositions which comprise a protein component, wherein the SRT can comprise a portion of the protein component, or the SRT can be the only protein in the protein component. In embodiments, the protein component can comprise, consist of or consist essentially of SRT. Consisting essentially of SRT means the protein component can include other, non-protein compositions, such as trace impurities.

It is expected that SRT obtained from any squid can be processed for use in the invention. In certain embodiments, the SRT can be isolated from any of the six squid species: *Loligo vulgaris, Dosidicus gigas, Sepioteuthis lessoniana, Todarodes pacificus, Illex argentinus, Omnastrepes bartami*, or a combination thereof. These six species represent a major portion of the global squid catch. Squid for production of SRT can also be farmed using various aquaculture techniques. In certain embodiments, the SRT are extracted from European squids (*Loligo vulgaris*). For this approach, SRTs are isolated from squid suckers, which are located along the muscular arms and tentacles. Separating SRT from the squid can be performed by providing a squid, and separating the SRT from the squid using any suitable technique. For example, separating SRT from squid can be performed according to techniques used in the art which are known from preparing squid for human or non-human animal consumption. The SRT can be stored at refrigerated temperatures or on ice prior to processing according to the invention. SRT can also be frozen and/or freeze-dried. SRT that is merely separated from squid, without further processing as described herein, is not included in the invention.

As an alternative to separating SRT from squid, the disclosure includes recombinant production of SRT. Thus, in various embodiments, SRT protein for processing according to this disclosure is produced using any suitable expression system, including but not necessarily limited to eukaryotic and prokaryotic expression systems, such as bacterial, yeast, mammalian, plant and insect expression systems. Many suitable expression systems are commercially available and can be adapted to express the SRT proteins. In general the expression vector will include at least one promoter driving expression of the SRT mRNA, and may include other regulatory elements to effect and/or optimize expression of the inserted SRT protein. The promoter can be a constitutive or inducible promoter. Suitable expression vectors can thus comprise prokaryotic and/or eukaryotic promoters, enhancer elements, origins of replication, selectable markers for use in maintaining the expression vectors in the desired cell type, polycloning sites, and may encode such features as visually detectable markers. More than one promoter can be included, and more than one SRT protein can be encoded by any particular expression vector, as desired. The expression vectors can also be adapted to express SRT-fusion proteins. The fusion proteins can include any other amino acid sequence that would be desirable for expressing in the same open reading frame as the SRT protein, and can include but are not limited to amino acid sequences involved in facilitating protein isolation and/or purification, such as a HIS-tag, of for solubility, secretion, or any other function. The SRT can be configured N-terminal or C-terminal to the fused open reading frame, depending on the particular fusion protein to be produced.

The present disclosure includes isolated cDNA encoding the amino acid sequences of SEQ ID NO:1 and/or SEQ ID NO:2 and expression vectors which comprise any polynucleotide sequence that encodes either of those proteins, and all such sequences are included in the scope of the invention. Thus, in one embodiment, the invention provides an isolated cDNA encoding either protein. In embodiments, the disclosure includes expression vectors comprising a polynucleotide sequence encoding at least one SRT polypeptide. The invention includes cells into which such an expression vector has been introduced, including in vitro cell cultures of any kind, such as prokaryotic, eukaryotic and insect cells. Irrespective of how the synthetic SRT proteins are expressed, the invention includes isolating the synthetic SRTs from the expression system using any suitable technique, and includes purifying them to any desired degree of purity. In additional embodiments, it is considered that the expression vectors can be configured to express more than one distinct SRT polypeptide. For example, in various embodiments, a single expression vector can encode more than one distinct SRT polypeptide by use of distinct cloning sites, or by designing a multi-cistronic mRNA with, for example, an internal ribosome entry site so that distinct polypeptides can be translated separately, but from the same mRNA. In other embodiments, the invention can include a separate expression systems, wherein for example a first expression system includes cells into which a first expression vector encoding a first SRT has been introduced, and a second expression system comprising cells into which a second expression vector encoding a second SRT has been introduced. In this manner, the first and second SRT proteins can be expressed and isolated, and if desired, combined to provide a composition comprising at least two distinct, synthetic SRT proteins. Such compositions can be processed, by for example, forming a melt comprising the at least two polypeptides.

To provide a non-limiting illustration of making SRT recombinantly, we used a multi-step transcriptome and proteomics approach to determine two representative SRT amino acid sequences, one from *Loligo vulgaris* and one from *Loligo pealei*. In embodiments, the amino acid sequence of the SRT protein that is processed according to this disclosure can comprise or consists of one of the amino acid sequence presented in FIG. 2. The *Loligo Vulgaris*-SRT-50 amino acid sequence is presented as SEQ ID NO:1; the *Loligo Pealei*-SRT-50 amino acid sequence is presented as SEQ ID NO:2).

A photographic representation of electrophoretic separation of the RACE products made in determining the *Loligo Vulgaris*-SRT-50 amino acid sequence, along with size markers is shown in FIG. 11A. This technique permitted identifying the cDNA that encodes the open reading frame for the *Loligo Vulgaris*-SRT-50 amino acid sequence. The cDNA was cloned into a commercially available pET14b vector system and transformed into *E. coli* strain BL21 (DE3). Recombinant SRT expression was produced and isolated, and its size was confirmed via an SDS-page gel as navigating with a molecular weight of 53 kDa. Recombinant SRT, with and without the signal peptide, was expressed as a fusion with the native His-tag found in the pET14B vector. Purification using nickel affinity chromatography gave higher yields and expression was confirmed via a SDS PAGE/Western blot. A photographic representation of recombinantly expressed SRT is presented in the SDS-PAGE separation in FIG. 11B and demonstrates production of the recombinant SRT with a molecular weight that is the same as a native SRT isolated from squid. The sequence of the recombinant SRT is provided as SEQ ID NO:1. The cDNA sequence encoding SEQ ID NO:1 is: provided as SEQ ID NO:3.

Processing the SRT can include a variety of manipulations. In various embodiments, the processing includes forming particles from an intact SRT, wherein the particles are suitable for heating to form a melt. For instance, particles can be formed by providing an intact SRT, or one or more non-particulate fragments of an SRT, and disintegrating such SRT samples into particles. The SRT may be disintegrated by grinding, granulating, powdering, cracking, crushing, micronizing, pulverizing, or any other technique suitable for disrupting the SRT such that particles are formed. The particles can be provided in any desirable size and shape, including but not limited to particles formed as rods, grains, granules, flakes, spherical particles, microparticles, nanoparticles, and any other particle shape. The particles can have any desirable dimension (s), including any measurement that includes particle diameter, length, width or weight, and can be prepared in mixtures or blends of SRT particles comprised of any particle size distribution, and for more than one source of SRT (i.e., combinations of SRT obtained from different squid species). In one embodiment, the invention provides particularized SRT that is pourable. In embodiments, the SRT can be provided in solution, in suspension, or in a slurry.

In one embodiment, the invention provides a particulate SRT, wherein the particulate SRT is provided in packaging. The packaging can comprise a container, or can itself be a container. Any suitable container can be used, such as a plastic or glass container, including but not limited to plastic or glass vials, jars, bottles, buckets, bags, packets, or any other suitable container. In various embodiments, the invention provides a product which comprises a sealed container comprising a particulate SRT, wherein the container includes printed material. The printed material can be part of the packaging, or it can be provided on a label, or as paper insert or other written material included with the packaging. The printed material provides information identifying the contents of the package, and instructs a consumer how to use the particulate SRT to form a SRT melt. The printed material can further comprise information such as to how to process the protein melt into any article of manufacture, embodiments of such processing and articles being further described herein.

In one aspect, the invention provides a composition comprising SRT protein(s), wherein the composition is held for a period of time at an increased temperature sufficient to form a melt. Methods for increasing the temperature of any processed SRT, as well as suitable temperature ranges for achieving various objectives of the invention, are described further below, and include but are not limited to subjecting the SRT to microwave heating, resistive heating, optical based plasmonic heating, conductive heating, and infrared heating. The melt could be heated using water as a solvent, but this temperature could be adjusted depending on the polar solvent used. As noted above, the maximum temperature is 195° C. above which point the SRT denatures Timing of the heating can be important, such as when spreading a melt, which is on average 1 micron per seconds. The disclosure includes subjecting the SRT protein to a heat treatment for any period of time, from 10 seconds, up to 24 hours, inclusive, including all time periods there between. While it is believed that the temperature ranges for formation of a melt will be applicable for any SRT that is obtained from any squid or produced recombinantly, the glass transition temperature for an any SRT composition can be measured using methods known in the art such as, for example, elastic modulus, E', onset criterion or Dynamic Scanning calorimetry (DSC).

In an embodiment, the composition (e.g., an SRT composition in a powder form) is melted by heating the composition to a temperature greater than the glass transition temperature of the composition (Tg), shaped into a desired three dimensional form as described further below, and cooled to a temperature below the Tg of the composition. The composition in various embodiments maintains the three dimensional form after cooling.

In one embodiment, the composition retains substantially all of its functional properties after melting and solidifying (e.g., physicochemical properties including but not limited to stiffness, modulus, chemical resistivity, shock absorbance, optical reflectivity). By "substantially" it is meant that a functional property does not change by more than 5% after a melting and cooling step.

Without intending to be constrained by theory, it is considered that the effect of temperature on bioelastomers can be classified into two categories. These are the relaxation of the physically entangled or chemically crosslinked protein structures above Tg and the irreversible aggregation above denaturation temperature, Td. When heated under dry conditions to above 195° C., SRT bioelastomer denatures. However, if the heating is performed in a polar liquid (e.g. water), the SRT bioelastomer flows like a viscoelastic liquid and can be molded and extruded. This recyclability can be exploited to mold the protein into flat thin films or into any three dimensional geometry, from simple rectangular ribbons to lithographic patterns and even into nano-scale objects such as nanotube arrays by a nanowetting process. In one embodiment, a method of the invention comprises providing a composition comprising or consisting essentially of or consisting of SRT, heating the composition to form a melt, and processing the melt, including cooling the melt, so that it forms a product, such as a three-dimensional article of manufacture. In embodiments the product retains the capability of reversible transition to a melt. In embodiments the disclosure includes making a product by extruding the SRT protein melt, electrospinning the SRT protein melt, coating the SRT protein melt onto a surface, molding the SRT protein melt, forming an adhesive layer, forming a film, fiber, ribbon or tube, and forming a film, such as forming a film on patterned surface.

In various embodiments, the compositions of the invention can include additives. For instance, an SRT melt could be mixed or blended with any desirable ingredient, such as a dye or other colorant, a pharmaceutical agent, an adjuvant, a plasticizer, a resin, a salt, carbohydrates, polysaccharides, wetting agents, any other organic or non-organic polymers or combinations thereof, minerals, steroids, growth factors, plant products, vitamins or any nutraceutical agent(s), lipids, oligonucleotids, glycans or mixtures of other bioelastomers including but not limited to silk, elastic, abductin, resilin and combinations thereof.

In various embodiments, forming a three-dimensional article according to the invention is performed using a solvent free process. For example, an SRT melt could be made into passive structures (nanotubes, micropatterns), stimuli responsive structures (e.g. pH or temperature responsiveness by mixing with other synthetic or biological polymers) or adaptive structures by self assembly via dissolving the SRT in weak acid and recrystallizing it using nanoscale domains of seeds that can be of biological or synthetic origin.

In various embodiments, the invention includes making a component of a pharmaceutical preparation that is formed using a protein melt of the invention. For example, a composition of the invention could be provided in tables, caplets or capsules and the like for a variety of purposes, such as for affecting the rate of release of the active ingredient, or as an enteric coating, or to improve pharmacokinetics generally. For example, a pharmaceutical composition could be added to a melt of the invention, and then solidified into any solid dosage form.

In embodiments, the disclosure includes forming a material that is cohesive and/or adhesive. As will be recognized by those skilled in the art, in general, cohesion is a property of like molecules to stick to each other due to mutual attraction. Adhesion is a property of different molecules or surfaces to bond to each other. In one embodiment, the disclosure includes an adhesive that is stable underwater for at least two months. In one embodiment, an adhesive film is provided. In embodiments the underwater adhesion strength of the film is approximately 1.5 MPa. In embodiments, articles of manufacture having a surface coated with the adhesive are provided. In embodiments, the adhesives are used in freshwater, brackish, or saltwater environments. In embodiments, the adhesives are coated onto a surface, such as the surface of an object. In embodiments, the adhesives are provided in a form suitable for any application which requires a wet adhesion, including but not necessarily marine applications, underwater welding environments, parts of boats or ships, recreational water craft, underwater columns that support peers or other structures, underwater drilling, swimming pools, aquaculture environments for production of fish or crustaceans, biofuel production environments, such as algae ponds which produce useful hydrocarbons, fishery related implements, such as nettings, submarine exteriors, underwater military implements, scuba and/or snorkeling equipment, surfing equipment, underwater audiovisual devices, such as underwater cameras and microphones, underwater lighting, food manufacturing environments, including but not limited to vats or other containers used for food and beverage processing, and other applications in the medical field, including but not necessarily limited to dental resins, bone repair, bandages for wound healing, and surgical sutures in the body, or any other implantable medical device that requires wet adhesion.

It will be apparent to those skilled in the art from the foregoing and the Examples presented herein that in various embodiments the present disclosure involves analysis and description of the interplay between nanoscale domains and chemistry for the adhesion of a protein melt and therefor can be used to provide the aforementioned novel coatings in the form of adhesives, such as those used for underwater applications, colloids and fibers, which can be used in the context of tissue engineering scaffolds, 3D printing for micro fabrication, surgery staples or sutures, or carrier particles for drug delivery, composites materials, such as composite biological materials with lipids, glycans, nucleic acids, other proteins, and synthetics, which can include but are not necessarily limited to resins, metals, polymers, and ceramics. It will also be apparent that compositions and method described herein can be used in the context of recombinant protein expression so that new and useful compositions of matter can be provided, which include but are not necessarily limited to chimeric proteins, and expression in plant systems for energy and food use. In embodiments the disclosure also provides SRT nano particles as drug delivery platforms, chimeric protein scaffolds, electrospin SRT as a controlled fiber and nano particles, and SRT/polysaccharide mixtures. In embodiments, the disclosure includes formation of compositions comprising at least one pharmaceutical agent and a composition formed using a protein melt as described herein.

Properties of the SRTs used in the invention can be determined using any suitable technique. Any SRT isolated from a squid as described herein can be analyzed by, for example, separating and/or isolating the SRT protein components. In one embodiment, a method of analyzing a SRT for use in the invention comprises separating an SRT from a squid and dissolving the SRT. SRT can be dissolved in a variety of solvents as further described herein. In one embodiment, the SRT is dissolved in a solution comprising an acidic component, such as in a weak acid. In one embodiment, the acid is a carboxylic acid, such as acetic acid. In one embodiment, the SRT is mixed with a polar solvent, such as water, wherein the polar solvent behaves like a plasticizer. The solution comprising an organic solvent can also comprise a denaturing agent, such as urea. A solution comprising SRT can be subjected to further processing, such as by separating SRT proteins based on size and/or charge. In one embodiment, the SRT composition is processed using gel electrophoresis, such as sodium dodecyl sulfate polyacrylamide gel electrophoresis (SDS-PAGE).

Separated SRT proteins can be further processed by, for example, excising the portion of a gel to which the proteins migrated, and separating the SRT proteins from the polyacrylamide gel components. The weight of any SRT protein used in the invention can have any weight as further described herein and in the Figures. In certain embodiments, the SRT comprises protein that migrates with an apparent molecular weight of approximately 50 kDa, or a protein that migrates with an apparent molecular weight of approximately 39 kDA, or 30 kDa, or a combination of such proteins.

The compositions of the invention can also be characterized by multiple criteria and analytical techniques, which include but are not necessarily limited to: i) molecular composition of SRT, which is ascertained using known molecular biology protocols (e.g., SDS PAGE for molecular weight, RNA/DNA sequencing to deduce amino acid composition, and mass spectroscopy for proteomics data); ii) materials science techniques (e.g., spectroscopic and scattering techniques); iii) morphology, which includes but is not necessarily limited to determining the size of ordered and amorphous domains, which can be performed using small angle neutron scattering (SANS) and atomic force microscopy (AFM); and iv) determining secondary structures, which can be characterized by using such techniques as Fourier transform infrared (FTIR) and Raman spectroscopy.

In general, it is considered that the structural, mechanical and physical characteristics of SRT as described herein are retained over at least one, and over multiple iterations of transition to melt and cooling/solidifying. In this regard, melted and reformed the same SRT compositions for a significant period of time, and it is likely that the transition to melt/cooling and solidifying process can be performed for any given composition is in the thousands of times, and this is assuming there is an upper limit, which is not necessarily the case.

The following specific examples are provided to illustrate the invention, but are not intended to be limiting in any way.

EXAMPLE 1

Figure 1:
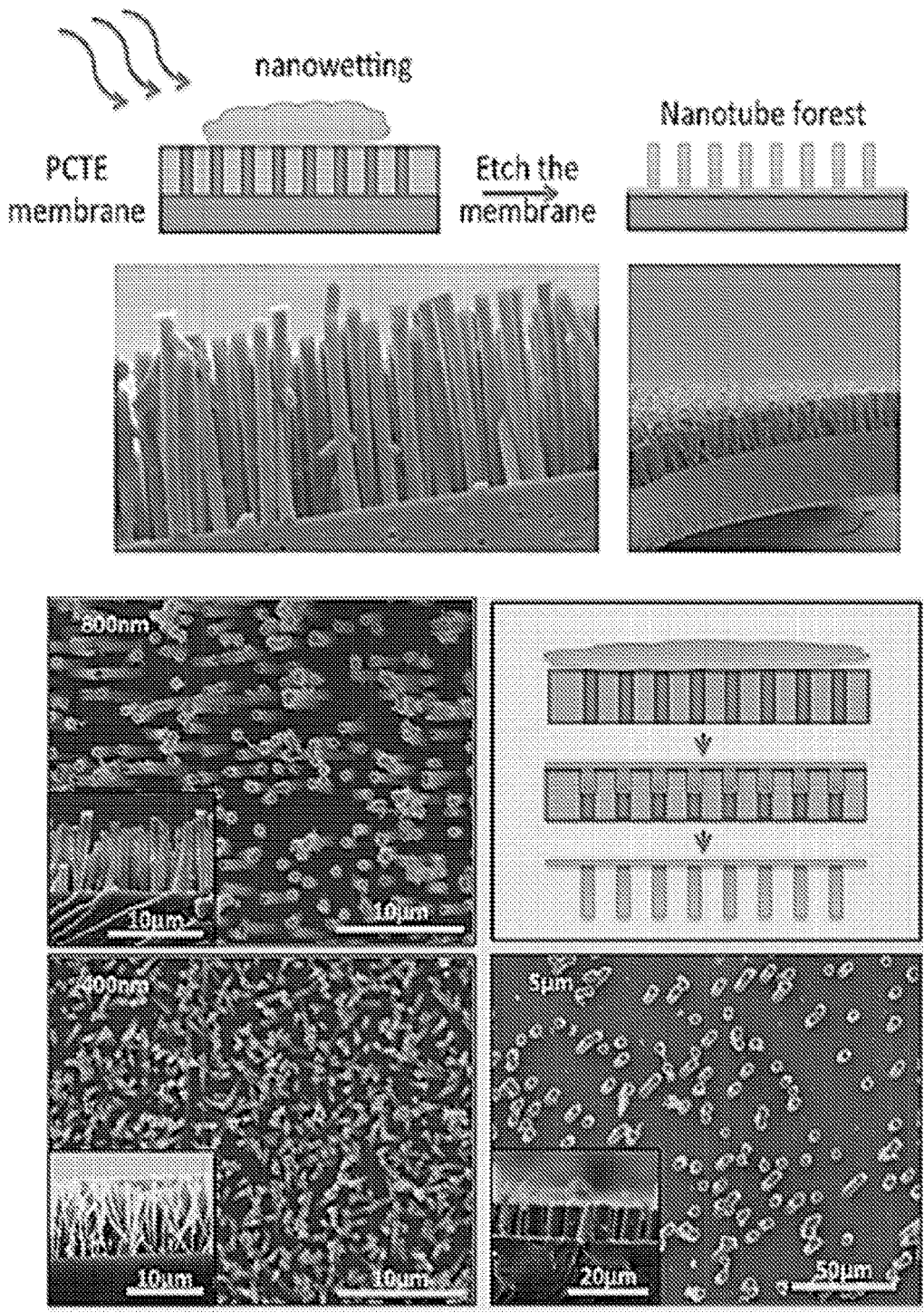
FIG. 1. Schematic and scanning electronic microscopy (SEM) representations related to solvent-free processing of SRT. Microwave heating of crushed SRT enables the processing of nanopillars. SEM observation of SRT nanopillars formed by depositing molten SRT on polycarbonate track etched (PCTE) membranes followed by template removal with dichloromethane. SRT nanotubes fabricated via nanowetting process in polycarbonate track etched (PCTE) membranes with varying diameters (400 nm, 800 nm, 5 µm)

We tested the SRT to determine whether it could be processed easily into different shapes by heating crushed SRT in a small volume of water by microwave (FIG. 1). In an embodiment the water is considered to be a plasticizer. The powdered SRT mixture melted into a liquid film, which could subsequently be processed into nano-patterned surfaces by, for example, a template wetting technique allowing formation of nano-pillars using a polycarbonate track etched (PCTE) membrane template (FIG. 1).

EXAMPLE 2

Figure 4:
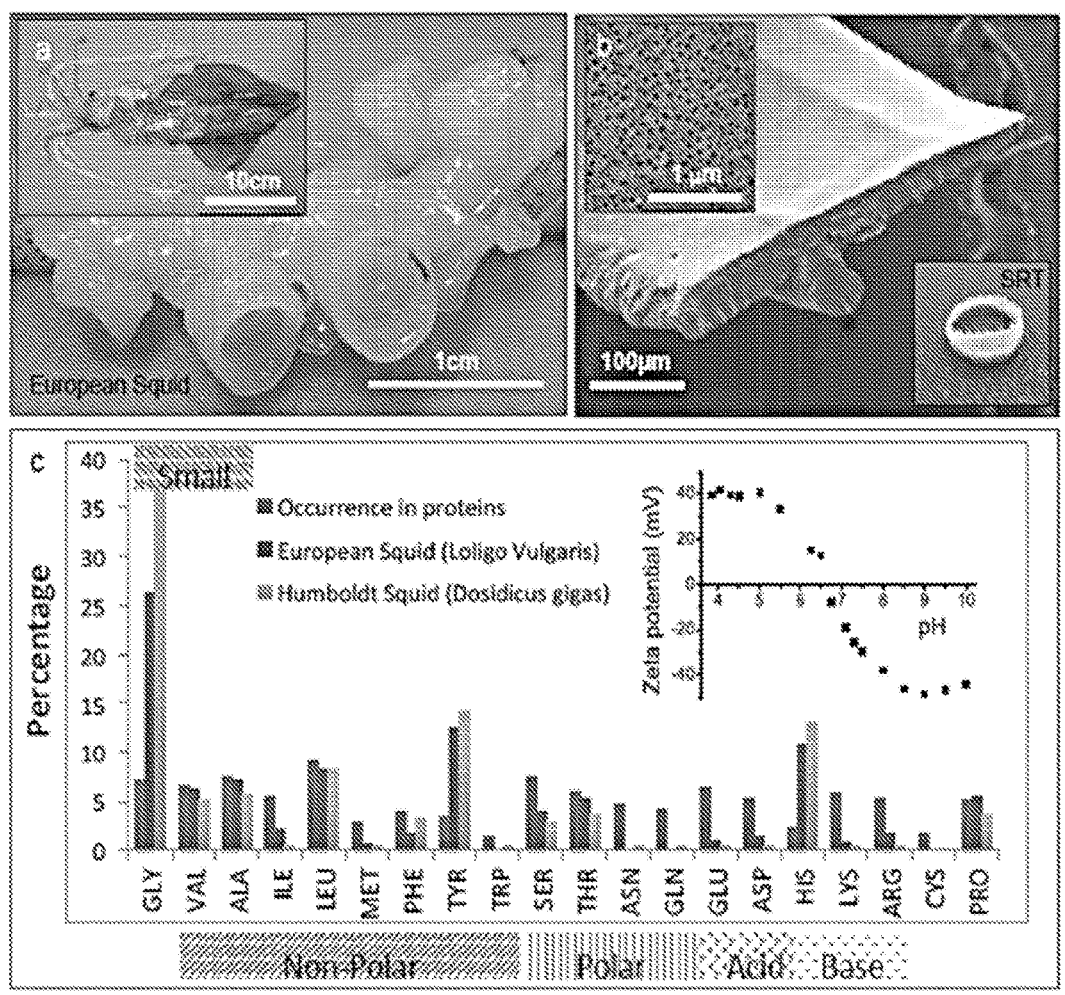
FIG. 4. European squid (*loligo vulgaris*) (a) captured in catalan waters (inset), shows a close-up picture of the suckers located in the tentacles, which contain the proteinaceous SRTs. (b) Cross-sectional SEM and optical image reveal a highly organized structure of nanopores and a ring structure respectively. (c) Amino acid composition of SRT from *Dosidicus* and *Loligo* squids are compared with commonly observed amino acid composition in eukaryotic cells. The inset shows the isoelectric point (pH=6.7) and zeta potential as a function of pH for the protein-melt extracted from the European SRT.

We studied the SRT extracted from European squids (*Loligo vulgaris*) obtained from squid as describe in Example 1. The SRT composition is wholly proteinaceous, which are stabilized by hydrogen bonding and hydrophobic interactions. FIG. 4 shows optical image of SRT (i.e., ring structure). This internal structure consists of an array of aligned nanotubes with an average diameter of 160±33 nm.

EXAMPLE 3

It should be noted that preparation of SRT films is an easy and recyclable process. Briefly, the SRT powder is placed in a glass slide with a small drop of deionized water above its $T_g$. The powder is gently pressed using a PDMS molds in order to shape the protein into different geometries as shown in FIG. 2.

EXAMPLE 4

Figure 3:
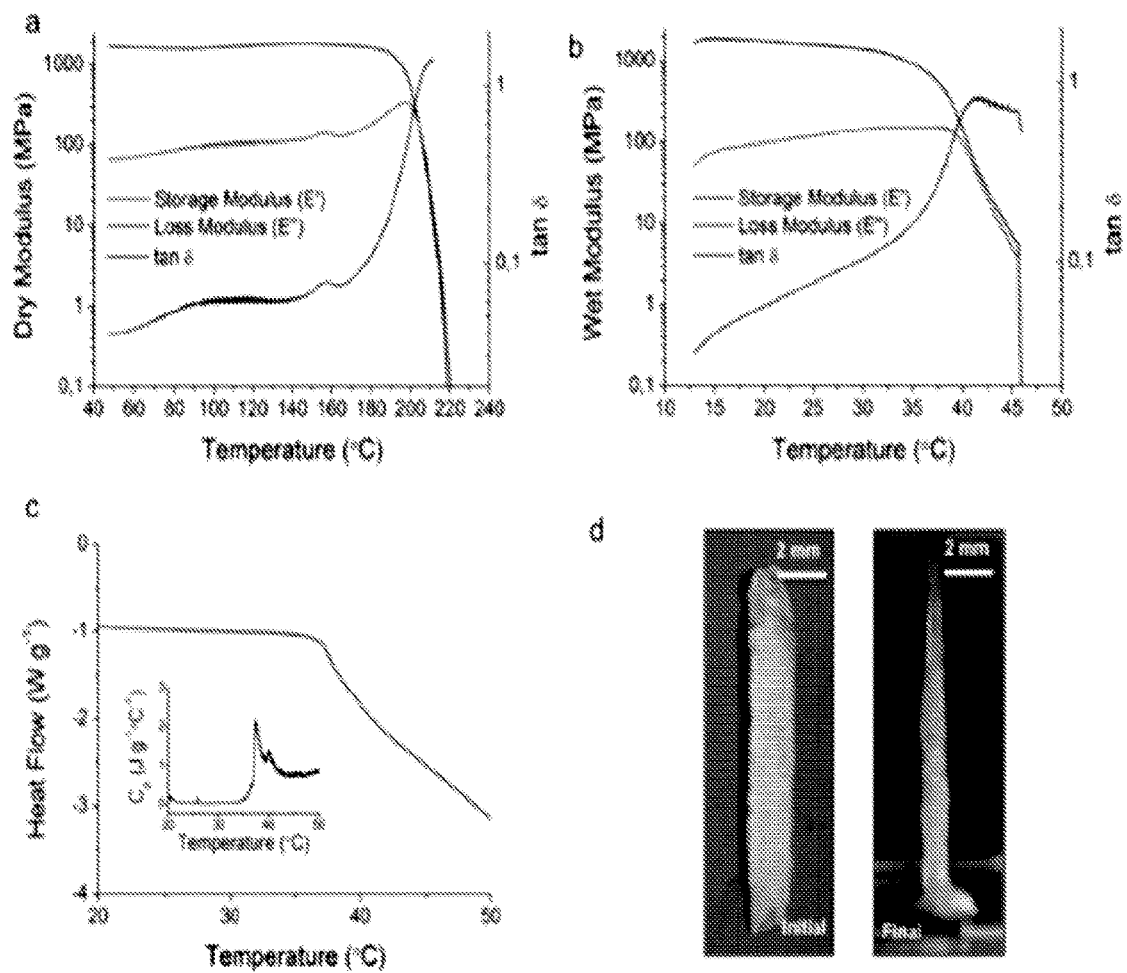
FIG. 3. (A) DMA oscillatory temperature ramp in dry conditions. The protein exhibits a stable mechanical behavior below 195° C., experimenting a sharp drop at 210° C. DMA oscillatory temperature ramp in wet conditions (B) reveal a phase-transition behavior of the protein film around 35° C., where the protein begins to flow (C) and the modulus decreases. DSC data shows the glass transition at 37° C. The pictures in (D) show the sample deformation due to the flow of the protein before and after the temperature ramp experiment.

This Example describes dynamic mechanical analysis of the compositions of the invention. The viscoelastic characteristic of the European SRT film was studied by Dynamical Mechanical Analysis (DMA). SRT were molded into thin ribbons to perform the experiments. DMA test is repeated after melting cycles and no differences are observed on the dynamic elastic modulus for wet (1.93±0.1 GPa) and dry (1.10±0.1 GPa) conditions under glass transition temperature, Tg. Similar elastic modulus has been reported for Humboldt SRT (i.e., 5.0 and 2.5 GPa for wet and dry respectively) in its native form. In the rubbery state (i.e., above glass transition temperature), the elastic modulus is 10 MPa, which is similar to other amorphous bioelastomers such as elastin. It is important to note that after multiple recycling of the protein, original stiffness value is retained in both dry and wet conditions. This is a unique advantage compared to other bioelastomers such as silk, for which the elastic modulus drops significantly for the wet condition due to the swelling and relaxation of non-crystalline beta sheet domains. The dry modulus (FIG. 3a) presents a stable modulus over a large range of temperature (25 to 195° C.), and the modulus sharply drops at the denaturation temperature, $T_d$=210° C. The storage modulus for the wet sample slowly decreases with time until it reaches the transition temperature (FIG. 3b). At this temperature, the protein film starts to flow (FIG. 3c), and the modulus drops eight orders of magnitude. The transition temperature is determined to be 36° C. according to the E' onset criterion (i.e., the point where the modulus starts decreasing), 41° C. according to the peak in tan δ and 45° C. according to the Born criterion for melting temperatures (i.e., the film no longer has sufficient rigidity to mechanically withstand the load). The transition temperature is confirmed by DSC (FIG. 3d), showing a peak in the $C_p$ (i.e., second order transition) at 37° C.

EXAMPLE 5

This Example illustrates, among other items, the interplay between nanoscale domains and chemistry for the adhesion of a protein melt.

Natural elastomers made from protein extracts have received significant interest as eco-friendly functional materials for underwater adhesion. In this Example we demonstrate a new adhesion mechanism based on nanoscale domains in the elastomeric structure of the protein complex and interface chemistry. To make the compositions described in this Example, SRT was extracted from European squid (*Loligo vulgaris*) ring teeth (SRT) and processed to create a protein melt via thermal treatment. An invertebrate in the cephalopod class in the phylum Mollusca that uses its limbs and suckers for a variety of tasks including holding prey, locomotion, and behavioral displays in cold sea water (i.e., 5-15° C.), squids have evolved teeth inside their suckers, which serve to swiftly grasp preys underwater. Typically, the muscles on the squid limbs generate large pressure differences at the suckers for holding a wide variety of objects. Although SRT are strictly made of proteins which are likely stabilized by hydrogen bonding and hydrophobic interactions, it is mainly functional in cold seawater with no known functions at elevated temperatures (e.g., >25° C.) based on its attachment biomechanics.

EXAMPLE 6

Figure 5:
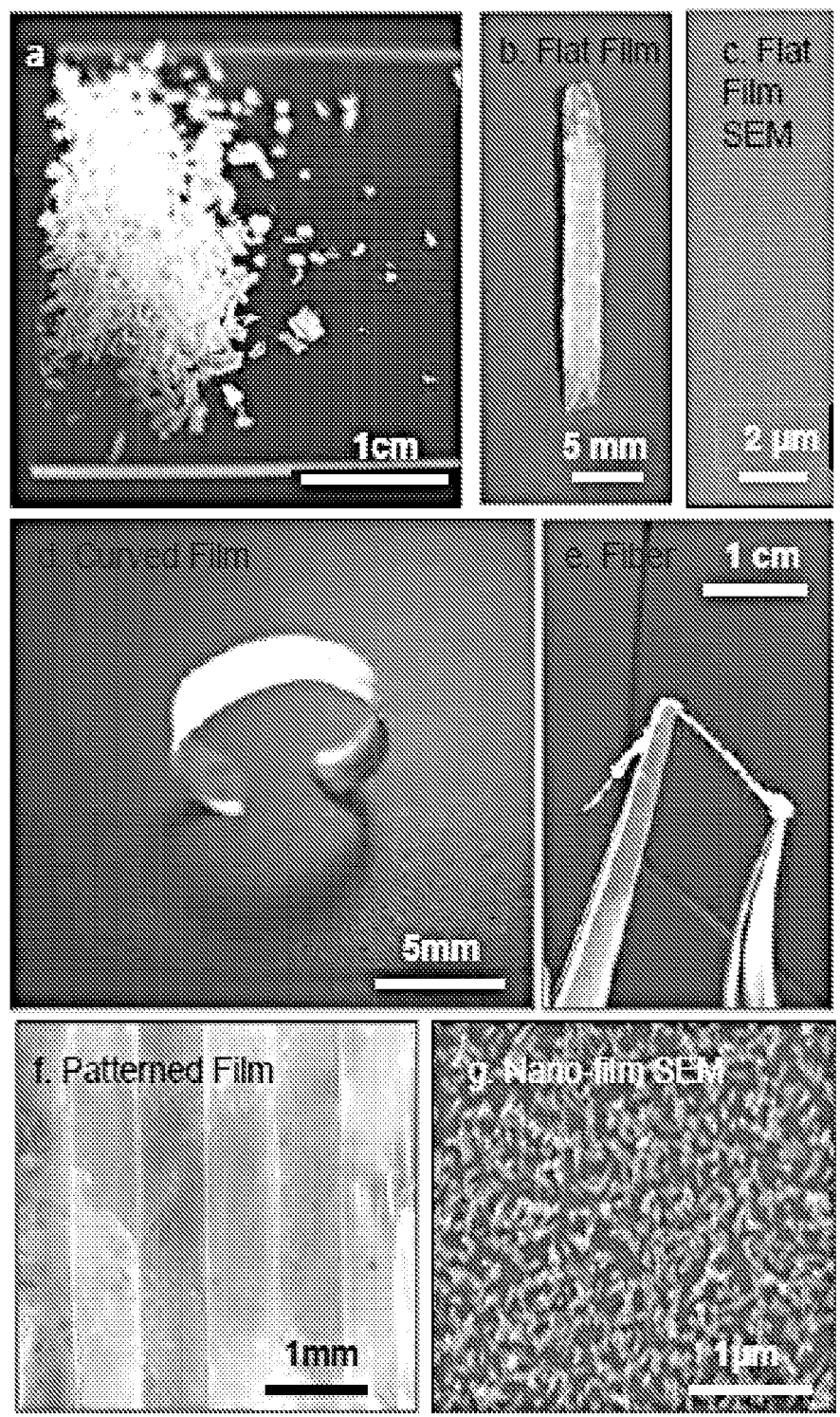
FIG. 5. Shaping and extrusion of the protein melt. The protein powder (a) is pulverized from SRT, and shaped into 3D geometries via a thermal process. Rectangular flat films (b), curved ribbon-like films (d), fibers (e), ridge-patterned films (f) or nanotube forests (g) are shown. SEM image of a rectangular film (c) reveals a smooth surface obtained by the melting process.
Figure 6:
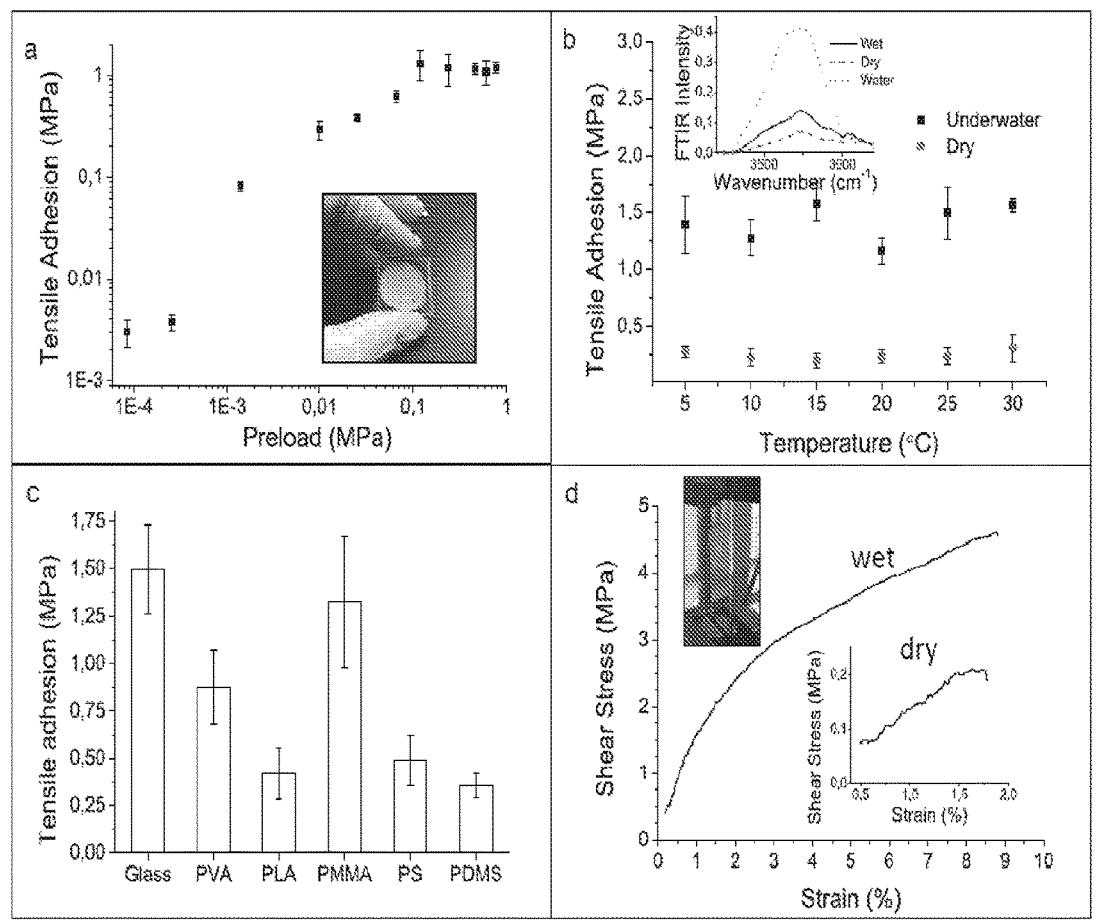
FIG. 6. Adhesive strength of the protein melt. (a) Tensile adhesion test is performed on protein melt between glass slides (inset) as a function of the preload. (b) The protein melt adhesion strength is measured underwater and dry conditions between 5 to 30 ° C. (b). Water content in the protein melt is characterized by FTIR in the —OH region (inset). (c) Underwater adhesion of the protein melt for various polymeric surfaces (i.e., polylactic acid (PLA), Poly(vinyl alcohol) (PVA), Poly(methyl methacrylate) (PMMA), Polystyrene (PS), polydimethylsiloxane (PDMS)) and its comparison for glass adhesion at room temperature. (d) Shear adhesion test and the corresponding setup for dry (inset) and wet conditions are shown.
Figure 8:
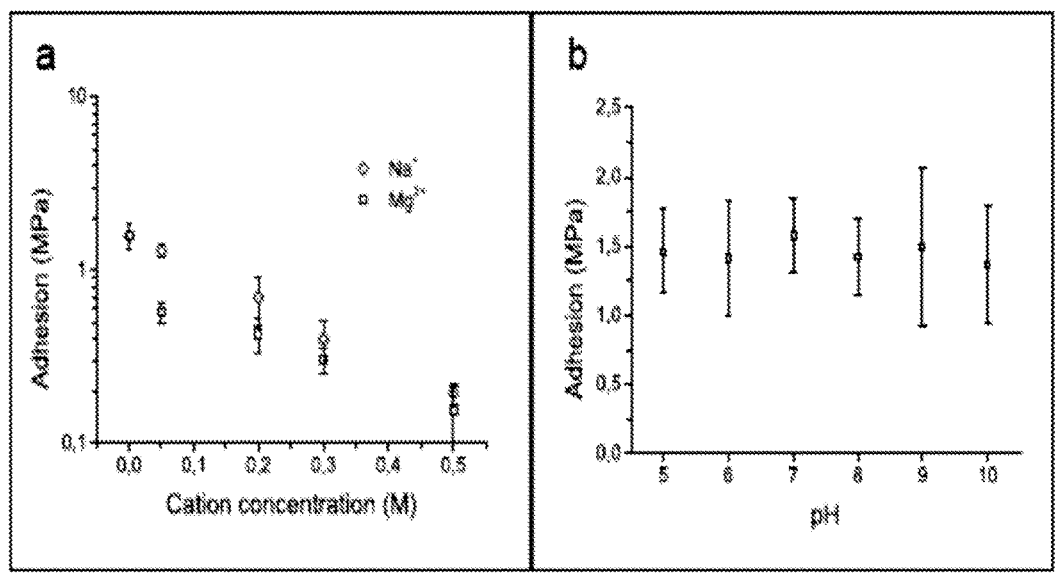
FIG. 8. Tensile adhesion data as a function of (a) salt concentration, and (b) pH of water solution. Ultrapure water is titrated with acetic acid and NaOH to prepare solutions between pH 5 to 10. NaCl and MgCl2 salts are added to ultrapure water between 0.05M to 0.5 M (Na+ and Mg2+) for salt concentration experiments. The protein film is kept immersed and tested in the respective conditions.

The SRT can be thermally processed to form a melt and shaped into any 3D geometry, such as films, ribbons, or tubes. The effect of temperature on the protein melt is similar to a polymer melt. As discussed above, when heated above 195° C., the protein melt denatures or oxidizes. The high temperature denaturation is most likely due to stabilization of the folding nuclei in the bioelastomer structure. However, if the heating experiment is performed in water (i.e., a plasticizer) at temperatures above the glass transition temperature but below the denaturation point, the bioelastomer flows like a viscoelastic liquid and can be molded and extruded. Preparation of the protein melt is an efficient and recyclable process. Briefly, the protein powder is extruded in deionized water above its $T_g$ to shape the protein melt into different geometries. The recyclability of the protein melt can be exploited by molding it into flat thin films or into any 3D geometry (FIG. 5), from simple rectangular ribbons to lithographic patterns and even into nanoscale objects for wetting applications. The protein melt shows a peculiar underwater adhesive response, although the native (i.e., prior to processing) SRT is not adhesive in water. The adhesion strength increases abruptly (i.e., two orders of magnitude) above a critical preload pressure, as shown in FIG. 6a. The adhesive strength is measured underwater at room temperature after curing the melt at 70° C. and pressing at varying preload conditions for one minute. Curing the protein melt at 45° C. provides similar adhesion strength but longer processing time is required. The adhesive is stable underwater at least for two months. When it is dried, both SRT and its melt adhere weakly to positively charged surfaces, such as branched polyethylenimine polyelectrolyte prepared via spin coating on a cleaned glass sample. In contrast, neither state shows adhesion to negatively charged polystyrene sulfonate at room temperature. FIG. 6b shows adhesion strength of the protein film as a function of temperature in dry and underwater conditions after curing both at 70° C. The dry experiment is performed after keeping the samples overnight in a vacuum desiccator. FTIR data shows the corresponding —OH peak region in the FIG. 6b-inset. FIG. 6c shows the adhesion data for various polymeric surfaces. PLA and PVA surfaces are tested without any treatment. Other polymeric surfaces (i.e., PDMS, PS, PMMA) are plasma treated to mimic the aging of the polymer (e.g., bacterial or enzymatic degradation) and the creation of hydroxyl sites on the polymer surface for improved adhesion. The adhesion in shear (i.e., ~2.5 MPa) is larger than that in tension for the protein film (FIG. 6d), which is common for soft materials. We have also performed experiments on the effects of pH and salt additions (FIG. 8), which show that the addition of salt substantially reduces the adhesion strength but pH has no effect on the adhesion strength in mild conditions.

EXAMPLE 7

Figure 7:
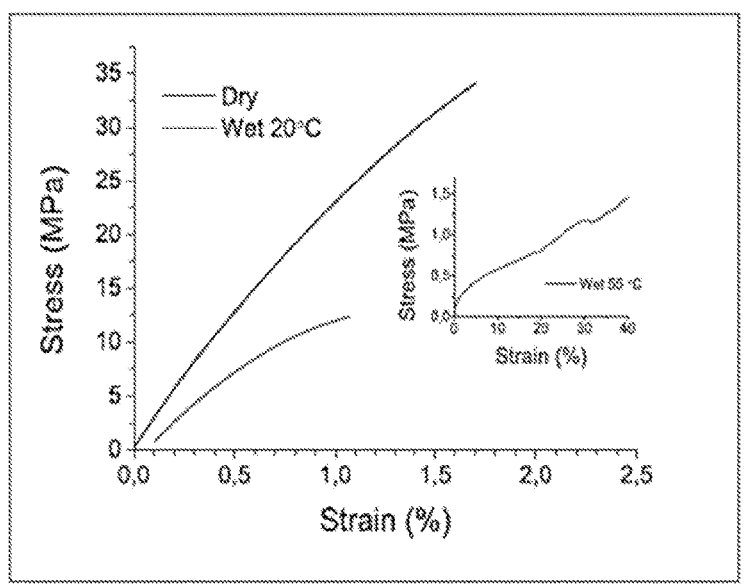
FIG. 7. Stress-strain curves for dry and wet protein film at 20° C. (<Tg) and for wet case (inset) at 55° C. (>Tg) are shown.

The viscoelastic characteristic of the protein film was studied using dynamical mechanical analysis (DMA), and the glass transition is analyzed using the differential scanning calorimetry (DSC). The protein melt is molded into thin ribbons to perform these experiments. The DMA test shows similar values for the dynamic elastic modulus in dry (1.93±0.1 GPa) and underwater (1.10±0.1 GPa) conditions at room temperature. The original stiffness value is retained in both conditions after multiple recycling of the protein. The dry modulus (FIG. 3a), which represents a stable modulus over a large range of temperature (25 to 195° C.), drops sharply above the denaturing temperature $T_d$=195° C. The storage modulus (i.e., elastic component) for the wet sample slowly decreases with time until it reaches the glass transition temperature (FIG. 3b). At this temperature, the protein melt starts to flow (FIG. 3c), and the modulus drops significantly. The modulus of the protein melt above $T_g$ is approximately 10 MPa (FIG. 7), which is similar to that of elastin. The glass transition temperature is 32° C. (FIG. 3d), showing a transition peak at $C_p$ (inset).

The following materials and methods were used to obtain that data presented in this Example and as otherwise indicated.

SRT Collection:

European squids (*loligo vulgaris*) are caught from the coast of Tarragona (Spain). The squid ring teeth (SRT) are removed from the tentacles and immediately soaked in deionized (DI) water overnight. After vacuum drying, the rings are pulverized in liquid nitrogen using a ceramic mortar and pestle.

SRT molding: 25 mg of SRT powder is mixed with 10 ml of deionized water at 70° C. (>Tg=32° C.). The mixture is gently pressed to spread into a flat thin film with an area of 1 cm², and then cooled at room temperature. The thickness of the film is approximately 200 µm. The powder may disperse during the melting process due to surface tension and capillary forces. If the film is not uniform, the thermal process could be repeated multiple times since the melting temperature is lower than the denaturation temperature ($T_d$=196° C.). The powder can be melted at temperatures lower than 70° C., but it may take a longer time (i.e., >1 minute) to complete the thermal process. Similarly, the protein film or the powder is extruded to different 3D shapes. For nanoforest fabrication, the SRT powder is melted for 1 minute in DI water on a polycarbonate track-etched (PCTE) membrane that has 400 nm of pore diameters (Sterlitech, Inc.), using a household microwave (2.45 GHz) oven. The microwave provides consistent homogeneous heating for melting the SRT powder on the PCTE membrane. After the deposition, PCTE membranes are immersed in dichloromethane (DCM) at 60° C. for 20 minutes, which dissolves the template and results in an open nanotube structure connected by a continuous backing of a protein film. The film is kept in ethanol and dried using critical point dying (CPD) to minimize bundling or collapse of the nanotubes.

Surface Characterization:

Top-view images of the protein film surface are collected using an atomic force microscope (AFM) in tapping mode (Digital Instruments Dimension Series 3100). AFM images are analyzed with WSxM software. RMS surface roughness is evaluated for 1×1 µm² and 10×10 µm² scan sizes. The surface morphology is also characterized by an electron microscope (Philips XL30) at an accelerating voltage of 5 kV.

Thermo-Mechanical Characterization:

Dynamic Mechanical Analysis (TA 800Q DMA) is performed in dry and wet conditions with film-tension and submersion-tension clamp modes, respectively. Sample dimensions are 15×2.5×0.2 mm³ for the dry test and 25×2×0 2 mm³ for the wet test. Stress-strain experiments are recorded at room temperature, with a strain rate of 1% per minute and a preload of 0.01N. Temperature experiments are recorded at 1 Hz, with an amplitude of 2 µm and a rate of 2° C. per minute.

Charge Measurements:

Two experiments are performed to measure the charge of the protein film. First, the charge of the film is qualitatively assessed on a charged substrate in the dry condition. Polyelectrolytes are prepared from branched PEI (Mw 750 000 g/mol), and from PSS (Mw~70 000 g/mol) solution by spin casting on glass substrates (VWR microslides). Second, the charge is quantitatively measured in water using a potentiometer. The ZetaSpin measures the zeta potential of a disk-shaped sample rotated at 1000 rpm using a conductivity probe. The protein film is melted on a 1-inch (in diameter) glass sample and pressed gently to spread the film uniformly. The pH probe is calibrated with standard solutions. The pH is varied by 0.5 units, and measured in the range of 3-11.

Adhesion Tests:

ASTM standard D1002 is adopted for the adhesion measurements. Tensile and shear tests are performed for the protein melt to estimate the adhesion strength. The protein film is sandwiched between two glass slides (1 cm$^2$ in area) for 1 minute using varying preloads at 70° C., and then, the preload is removed and cooled at room temperature. The film is dried overnight or kept in DI water before testing. The protein melt is also tested in tension for various polymers. PDMS and PS are plasma treated for 1 minute using a handheld laboratory corona treater (Electro-Technic products, model BD-20). For the tensile adhesion test, a homemade setup is built for both underwater and dry adhesion. The temperature is controlled with a custom-made peltier device. Vertical force, normal to the adhesion plane, is measured at the adhesion failure, and normalized by the adhesive contact surface area to calculate the adhesion strength. For the shear adhesion, samples are mounted in single-lap configuration and tested using commercial equipment (United Calibration Corp., STM-20) at 1.27 mm/min strain rate. The film is immersed in water until the testing, to ensure that the adhesive remains wet at all times, and maintained at 100% humidity during the shear test.

In this Example we demonstrate development of versatile materials fabrication techniques for an elastomeric protein extracted from SRT to produce colloids, thin films, fibers, and nanotube arrays. These materials have potential use in multiple fields including drug delivery, biomaterials coatings, tissue engineering, and adhesion. We demonstrate formation of such compositions using an approach that involves forming a melt, and another approach that does not rely on melt formation, but instead uses a solvent-based process.

As described in the foregoing Examples, SRT can be shaped into any geometry with a diverse array of processing methods. Using SRT powder as raw material, it can be thermally processed exploiting the reversible phase transition of the protein. Adjusting the temperature and humidity conditions, the SRT can overcome its glass transition temperature ($T_g$) and achieve a protein melt state. As a melt, the SRT exhibits a viscoelastic behavior, and flows under pressure, which is very similarly to thermoplastic polymer melts. Therefore, conventional processing approaches for thermoplastic polymers can be applied to this material such as injection molding, extrusion, annealing, and others.

In addition, the SRT protein can be dissolved in some organics (e.g., HFIP) and acidic or alkaline media. The protein structure of SRT is held together by weak forces (hydrogen bonding), and breaking these inter-domain hydrogen bonds can dissolve it. However, the protein can be recovered if the solvent is evaporated or solution is titrated to SRTs isoelectric point (i.e., pH=6.7). Therefore, SRT can be deposited as a thin film on surfaces via evaporation or titration.

Figure 9:
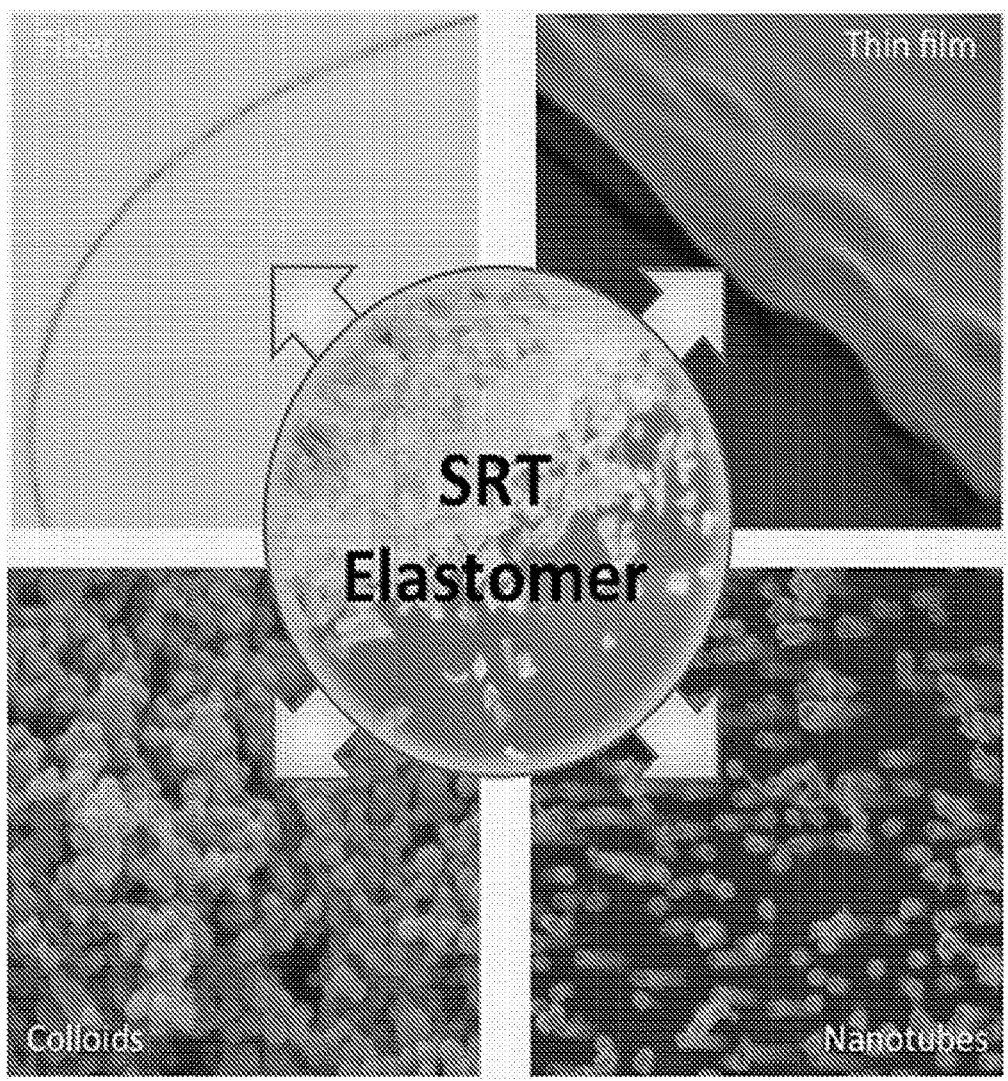
FIG. 9. Scheme for the fabrication of nanoscale objects from SRT elastomer.

The combination of the solvent-based and thermal based approaches open up a wide range of processing possibilities and applications, representative embodiments of which are demonstrated in this Example (see, e.g., FIG. 9). Additionally, SRT colloids can be created by ultrasonication from bulk phase or by surfactant induced aggregation from solution phase.

In this Example, SRT is extracted from European squid (*Loligo vulgaris*) ring teeth as discussed above and processed to create a protein melt via thermal treatment. Production of fibrous structures has potential in many applications such as membranes, tissue engineering scaffolds, sensors, protective clothing and many other applications. One efficient, reproducible, and cost effective way to produce fibers is through electrospinning (see FIG. 9). We demonstrate formation of SRT fibers through different methodologies and, without intending to be constrained by theory, believe we have optimized elongation and diameter of the fibers.

Different methods of fiber extrusion include melt (i.e., considered the simplest and least expensive technique), wet (i.e., fibers that require dissolving in solvent), dry (i.e., fibers with a melt temperature close to their thermal degradation temperature), dry-jet wet (i.e., high performance fibers with a liquid crystal structure), and electro spinning. In this example, SRT fibers were obtained via electro-spinning. Formation of these fibers was tested through three methodologies to optimize the elongation of the fiber and to control its diameter. All mixtures are spun at a 3 mL/hr feeding rate at 10 kV voltage, and the fibers are characterized on gold-coated glass slides using a scanning electron microscope. First, we dissolved SRT in 5% Acetic Acid/water (v/v) mixture. SRT is positively charged in this solvent and dissolves homogenously. Ethanol is added to the solution in equal parts to increase the yield of electro-spinning. However, the fiber density was low. Second, SRT is dissolved in Hexafluoro-2-propanol (HFIP), which is a good polar solvent (hydrogen breaker) for proteins (e.g., commonly used in amyloid research). The average fiber diameter measured to be 0.5 nm. Although, uniform fibers formation is observed in HFIP, this solvent has a high vapor pressure, and it is toxic. Therefore, we switched to Poly-ethylene-oxide (PEO), which is commonly used as a biomaterial due to its biocompatibility, hydrophilicity, and versatility. The fiber generated using SRT-PEO mixture, has the diameter of 2 µm. This method also provides formation of fibers without beads.

As discussed above, SRT is a strong candidate for protein nanoparticles applications because of its unique thermo-mechanical applications. When heated above its $T_g$ in aqueous solution, the SRT becomes very viscous (protein melt). Ultrasound is applied to the protein in these conditions and the bulk melt breaks into small particles due to its low elastic modulus. Adjusting the power and the exposure of the ultrasound, the breaking of the bulk melt into small particles can be controlled. Furthermore, the resulting particles can be separated by size by centrifugation, hence resulted in monodisperse particle distribution. Although the particles are considerably rough and non-spherical right after detaching from the bulk melt, the annealing of the particles can remove the surface defects. For this purpose, the particles are deposited on a flat substrate and annealed in hot water. The particles are re-shaped spherically because of the minimization of surface energy in water and the protein viscous state in water above Tg. This particle formation method exploits the reversible melt-transition of the SRT, enabling the top-down fabrication of particles with water as the only solvent (unlike the usage of organic solvents which is common it polymeric nanoparticle synthesis). The proposed method can generate particles in the nanometric size scale. (FIG. 9). The nanoparticle size can be controlled by adjusting the sonication parameters and by centrifugation for size separation. In addition, the particles are pH-sensitive since SRT is dissolved by high/low pH. 100 nm particles are easily dissolved in low acid concentration (addition of small volume of acetic acid). The size reported for 100 nm in radius colloids drops to 2 nm, corresponding to the dissolved protein (i.e. individual protein in solution).

We performed RNA sequencing to study the molecular composition of the SRT proteins obtained from the suction cups of *Loligo Vulgaris* and *Loligo Pealei*. A transcriptome library is created for individual species by de novo transcript assembly combined with mass spectroscopy analysis of the SRT peptides digested by an enzyme. We also used RACE-PCR to confirm the full-length transcripts. FIG. 2 lists the corresponding protein sequences for the two bands (~50 kDa).

In summary, we have demonstrated various approaches to create materials fabrication techniques for SRT protein. SRT is an eco-friendly material with remarkable mechanical properties. Its biocompatibility with controllable degradation rates from hours to years provides unique opportunities for a range of applications that are further described above.

The following materials and methods were used to obtain the data presented in this Example.

SRT Thin Films: SRT powder is dissolved in 5% acetic acid (v/v) solution (pH 3 approximately) or Hexafluoroisopropanol (HFIP) in a concentration of 4 mg/mL. The protein solution is pipetted on glass and silicon substrates and evaporated overnight resulting in a homogeneous protein thin film. Film adsorption to glass surface is measured by a WGM resonator with diameters around 350 μm which is evanescently excited via a tapered optical fiber, and recorded using Lab VIEW program.

Molding of SRT-Starch Composites: A PDMS mold of a master object is fabricated by immersing the object in PDMS before curing. The object is kept immersed in PDMS during the curing process and is carefully removed from the PDMS matrix, resulting in a two-piece PDMS mold. SRT powder is dissolved in 10% acetic acid in a concentration of 50 mg/mL. 3 g of commercially available corn starch is mixed in 20 mL of DI water with 5 mL of the protein solution. The mix is heated at 85° C. for 5 minutes while stirring, 1 mL of SDS 25 mM is added and the mix is heated at 85° C. for 10 more minutes. The mix is poured in the previously fabricated PDMS mold and it is heated in a household microwave for 30 seconds so the excess water evaporates. The full mold is cooled down at room temperature and the SRT-starch object is demolded.

SRT Particles: SRT powder is melted and pressed to form a thin film on a glass slide and immersed in 7 mL of ultrapure water at 80° C. After 15 minutes of stabilization, an ultrasonication head is dipped in the liquid and operated for 15 minutes at 60% of output power. The solution is centrifuged at 2000 rpm for 5 minutes and 50 μL of supernatant is are pipetted on a 1×1 cm glass slide and evaporated at room temperature overnight. Particle annealing: the glass with SRT particles deposited on top is immersed in ultrapure water at 80° C. for 20 minutes. Then the glass slides are dried overnight at room temperature. Particle dissolution: acetic acid (Sigma Aldrich reference) is added to the particle solution to 10% v/v concentration and it is stabilized for 5 minutes.

Electrospinning: A vertical electrospinning unit with a copper target is used for fiber formation. Briefly, SRT is dissolved in HFIP (Sigma Aldrich) solution with sonication to fully dissolve the SRT protein. Before electrospinning undissolved SRT clots were discarded by centrifuging the solution at 10,000 rpm for 5 mins. The clear solution is loaded into a glass 5 mL syringe and a 25G syringe needle is placed at the tip of syringe for electrospinning. The tip to copper target distance is 18 cm and the protein melt solution is loaded at a 6 ml/hr rate using a syringe pump (Harvard Apparatus, MA). The syringe tip electrospinning is initiated by charging the system at 10 kV voltage. Collected fibers are characterized using SEM.

SRT Dataset: European squid (*Loligo vulgaris*) dataset has been analyzed Euro-squid dataset contained 10,160,143 paired-end reads of 250 bp. Quality control was done using Trimmomatic. Adaptor sequences and polyAs were removed from reads. A sliding window trimming was performed, cutting once the average quality within a window size of 4 base pairs falls below 25. Very short reads of <36 base pairs were removed.

Transcript Assembly: the clean data set was assembled using Trinity with strand specific RNA sequencing library specification. 42937 and 33180 transcripts were assembled for MBL-squid dataset and Euro-squid datasets respectively.

Blast Search and Short Read Mapping: peptide sequences from the protein of interest were sequenced using mass-spectrometry. From this, peptides with a confidence score of >50 were searched against trinity-assembled transcripts using tblastn. The blast hits that had alignments with >90% of the length of the peptide and with >=80% sequence identity were identified as the best hits. These best-hit transcripts were again searched for beta sheets using tblastn. The identified transcripts that have both peptide and beta-sheet sequence match were chosen as candidate transcripts. However, since these were not full-length transcripts, further steps were performed to identify the full-length candidate transcripts. In order to identify the full-length transcripts, the clean data set was aligned to each of the candidate transcripts using bwa-mem algorithm. The resulting alignment file was parsed to identify the longest read that mapped to the end of the transcript and was further used to extend the transcript. The entire sets of reads were again mapped to the extended candidate transcript. This process of alignment and extension was repeated until a stop codon is encountered and the transcript is considered to be full-length.

Validation: the identified candidate transcripts were aligned using Clustalw. Further validation was done by checking the amino acid composition Amino acid composition of all the assembled transcripts were calculated and compared to that of the published data. The candidate transcripts had a composition similar to that of the published dataset.

5' and 3' RACE: To confirm the coding sequence of the Euro protein, a 3' and 5' Race was carried out using Clonetech's SMARTer™ Race cDNA Amplification kid (Clontech Laboratories, Mountain View, Calif.). The RT-PCR was carried out as specified by the manufacturer using 1 ug of total RNA for both the 3' and 5' Race. The resulting cDNA library from the 3' Race was used to amplify the open reading frame of the Euro gene using a gene specific 5' primer (5'-GCCATTTGATTAAGACATTTGGTCAAT-3' SEQ ID NO:4) that was specific for the predicted 5' UTR. The 3' primer was the universal primer mix (UPM) that was provided in the kit SMARTer RACE kit. The 5' Race library was used to confirm the 5' UTR using the gene specific 3' primer (5'-CCACCGAAAGCCCATCCCACTGGAG-GAAGA-3' SEQ ID NO:5), while the 5' primer was the UPM. The PCR products were cloned into the PCR4.1 TOPO vector using the TOPO TA cloning kit for sequencing (Life Sciences kit) by TA cloning and sequenced by Sanger Sequencing.

Cloning into pET14b Vector: The open reading frame of the Euro protein was cloned into NcoI/XhoI site of the pET-14b vector (Novagen). Due to the native NcoI site in the gene sequence, the compatible end restriction enzyme BspHI was used at the 5'end. Digestions of the PCR products and the vector were carried out at 37 C for 3 hrs. and purified using Qiagen PCR clean up (Qiagen). Purified PCR fragments were ligated using T4 ligase (New England Biolabs) with a ratio of 3:1 insert to vector. The gene was cloned in framed with the native ATG start codon of the pET-14b vector. The primers used to amplify the PCR product were: Forward primer 5'-TCATGATGGGAGCCATG-CAACTAGC-3' SEQ ID NO:6; Reverse primer 5'CTC-GAGCCCAATCCTC-AGTGTGTTACTGTATG-3' —SEQ ID NO:7.

Expression of Recombinant SRT: A single colony was inoculated and grown overnight in 25 ml of LB with ampicillin (50 µg/ml). The next day, the overnight culture was inoculated into four 1-liter shake flask culture containing 500 ml of LB ampicillin (50 µg/ml). The culture was grown at 37° C. until an OD600 of 0.6 and IPTG was added to obtain a final concentration of 0.5 mM for 4 h. The cells were pelleted at 10,000 r.p.m. for 15 min and washed twice with 10 ml of 20 mM Tris pH 8. The cell pellet was then resuspended in 50 ml of lysis buffer (50 mM Tris pH 7.4, 200 mM NaCl, 1 mM PMSF) and lysed using a high-pressure homogenizer. The lysed cells were pelleted at 19,000 r.p.m. for 1 h at 4° C. The pellet was then washed twice with urea wash buffer (100 mM Tris pH7.4, 5 mM EDTA, 2 M urea, 2% (v/v) Triton X-100, 5 mM DTT) and twice with wash buffer (100 mM Tris pH7.4, 5 mM EDTA, 5 mM DTT). The remaining pellet was then resolubilized in 20% acetic acid.

While the invention has been described through specific embodiments, routine modifications will be apparent to those skilled in the art and such modifications are intended to be within the scope of the present invention.

What is claimed is:

1. A method of making an amorphous product, the method comprising mixing a squid ring teeth (SRT) protein and a plasticizer to obtain a mixture of the SRT protein and the plasticizer, heating the mixture to between 32° C. and 195° C. to obtain an SRT protein melt, and forming the amorphous product from the SRT protein melt, wherein the forming the product is reversible, wherein the SRT protein comprises an approximately 50 kDa protein of squid ring teeth of *Loligo Pealei* or of *Loligo Vulgaris*.

2. The method of claim 1 comprising sonicating the mixture during or subsequent to the heating.

3. The method of claim 1, wherein the forming the product comprises extruding the SRT protein melt, coating the SRT protein melt onto a surface, molding the SRT protein melt, or a combination thereof.

4. The method of claim 3, wherein the method comprises heating the mixture to between 32° C. and 195° C. at least two times prior to the cooling the SRT protein melt.

5. The method of claim 1, wherein the forming the product comprises cooling the SRT protein melt to form at least one structure having a three dimensional shape.

6. The method of claim 1, wherein the forming the product comprises forming an adhesive and cohesive layer.

7. The method of claim 1, wherein the forming the product comprises forming a film, fiber, ribbon or tube.

8. The method of claim 7, wherein forming the film is performed, and wherein forming the film comprises placing the SRT protein melt on a patterned surface.

9. The method of claim 1, wherein the method comprises adding a carbohydrate to the mixture of the SRT protein and the plasticizer prior to or during the heating.

10. The method of claim 1, wherein the protein of squid ring teeth of *Loligo Pealei* comprises SEQ ID NO:1, or wherein the protein of squid ring teeth of *Loligo Vulgaris* comprises SEQ ID NO:2.

11. The method of claim 10, wherein the protein of squid ring teeth of *Loligo Pealei* or the protein of squid ring teeth of *Loligo Pealei* is present in the amorphous product, and wherein the protein squid ring teeth in the amorphous product was produced recombinantly before the mixing.

* * * * *

SEQUENCE LISTING

<160> NUMBER OF SEQ ID NOS: 7

<210> SEQ ID NO 1
<211> LENGTH: 559
<212> TYPE: PRT
<213> ORGANISM: Loligo Vulgaris

<400> SEQUENCE: 1

Met Gly Ala Met Gln Leu Ala Val Ala Leu Ile Val Leu Gly Ile Ser
1               5                   10                  15

Ser Ser Ala Asn Gly Ile Phe Asn Gly Ser Thr Ala Gly Leu Gly Ser
            20                  25                  30

Gln Pro Ser Pro Tyr Ile Gly Arg Ser Val Ser Thr Val Ser His Gly
        35                  40                  45

Ser His Tyr Pro Ala Tyr Gly Gly Trp Gly Tyr Asn Leu Gly Ser Trp
    50                  55                  60

Gly His Gly Leu Gly Gly Leu Gly Ser Tyr Gly Leu His Tyr Pro Met
65                  70                  75                  80

Ser Ser Ser Val Ser His Val Ser His Thr Ala His Ser Pro Leu Gly
                85                  90                  95

Tyr Tyr Gly Trp Gly Gly Tyr Gly Gln Gln Ser Pro Leu Thr His Val
            100                 105                 110

Ser Arg Thr Ala Leu Pro Pro Val Gly Trp Ala Phe Gly Gly Leu Tyr
        115                 120                 125

Arg Gly His Gly Ala Gln Val Ser Gln Ser Pro Val Arg Tyr His Gly
    130                 135                 140

Tyr Ser Phe Gly Arg Pro Ala Val Ala Thr Arg Arg Val Leu Tyr Pro
145                 150                 155                 160

Lys Pro Val Val Ser His Val Thr His Thr Ile Pro His Ser Gly Trp
                165                 170                 175

Gly Met Gly Gly Phe Gly Gly Tyr Val Ser Ser Tyr Pro Thr Gly Ala
            180                 185                 190

Ser Val Asn Thr Val Ser His Gly Ile Ser His Ala Pro Val Tyr Gly
        195                 200                 205

Gly Trp Gly Ala Gly His Ala Ile Ser Thr Val Ala His Gly Ile His

```
                    210                 215                 220
Pro Thr Val Thr Tyr Gly Gly Met Gly Leu Gly Gly Leu Tyr Gly Gly
225                 230                 235                 240

Tyr Gly Ala His Tyr Pro Ala Ser Thr Ser Val Ser His Thr Thr His
                245                 250                 255

Ser Val Pro His Thr Val Gly Leu Gly Leu Gly Ser Leu His Gly Gly
                260                 265                 270

Trp Gly Gly Tyr Gly Ile Gly Tyr Gly Val His Ser Pro Val Gly Ala
            275                 280                 285

Ser Val Ser Thr Val Ser His Gly Ile Gly His Pro Val Gly Tyr Gly
            290                 295                 300

Thr Trp Gly Leu Gly Ser Gly Ala His Tyr Pro Val Gly Gln Ser Val
305                 310                 315                 320

Ser Thr Val Ser His Gly Val His Ala Pro Val His Gly Gly Leu
                325                 330                 335

Gly Leu Ser Gly Ser Ser Val Ser Thr Val Ser His Gly Val Pro Ser
                340                 345                 350

Leu Gly Ala Tyr Gly Gly Tyr Gly Leu Gly Gly Leu Ile Gly Gly His
            355                 360                 365

Ser Val Tyr His Pro Thr Gly Ser Ser Ile Ser Thr Val Ser His Gly
370                 375                 380

Val Pro Ser Leu Gly Ala Tyr Gly Gly Tyr Gly Leu Gly Gly Leu Ile
385                 390                 395                 400

Gly Gly His Ser Val Tyr His Pro Thr Gly Ser Ser Ile Ser Thr Val
                405                 410                 415

Ser His Gly Val Pro Ser Leu Gly Ala Tyr Gly Gly Tyr Gly Leu Gly
                420                 425                 430

Gly Leu Ile Gly Gly His Ser Val Tyr His Pro Thr Gly Ser Ser Ile
            435                 440                 445

Ser Thr Val Ser His Gly Val Pro Ser Leu Gly Ala Tyr Gly Gly Tyr
            450                 455                 460

Gly Leu Gly Gly Ile Val Gly Gly Tyr Gly Ala Tyr Asn Pro Thr Gly
465                 470                 475                 480

Ser Ser Ile Ser Thr Val Ser His Gly Val His Ser Pro Val Gly Tyr
                485                 490                 495

Gly Gly Tyr Gly Leu Gly Gly Leu Ile Gly Gly Tyr Gly Ala Tyr His
                500                 505                 510

Pro Ala Gly Ser Ser Ile Ser Thr Val Ser His Gly Ile Asn Ser Leu
            515                 520                 525

Gly Ala Tyr Gly Gly Tyr Gly Asn Gly Gly Leu Leu Gly Gly Tyr Gly
            530                 535                 540

Val Pro Leu Pro Leu Ser Thr Thr Ser His His Thr Val Thr His
545                 550                 555

<210> SEQ ID NO 2
<211> LENGTH: 493
<212> TYPE: PRT
<213> ORGANISM: Loligo Pealei

<400> SEQUENCE: 2

Met Gly Ala Met Gln Leu Ala Val Ala Leu Ile Val Leu Gly Ile Ser
1               5                   10                  15

Ser Ser Ala Asn Ala Val Phe Asn Gly Ser Trp Val Gly Leu Gly Ser
            20                  25                  30
```

```
Gln Pro Ser Pro Leu Ile Gly Lys Ser Val Ser Thr Val Ser His Gly
             35                  40                  45

Tyr His Tyr Pro Gly Tyr Gly Gly Trp Gly Tyr Gly Leu Gly Gly Trp
 50                  55                  60

Gly His Gly Leu Gly Gly Leu Gly Ser Tyr Gly Leu His Tyr Pro Met
 65              70                  75                      80

Ser Ser Ser Val Ser His Val Ser His Thr Ala His Ala Pro Leu Gly
                 85              90                  95

Phe Ser Gly Trp Gly Gly Tyr Ala Gln His Ser Pro Leu Thr His Val
            100                 105                 110

Ser Arg Thr Ala Leu Pro Pro Val Gly Trp Ala Phe Gly Gly Ile Tyr
            115                 120                 125

Arg Gly His Gly Ala Gln Val Ser Gln Ser Pro Val Arg Tyr His Gly
            130                 135             140

Tyr Ser Leu Gly His Pro Ser Val Ala Thr Arg Arg Val Val Tyr Pro
145                 150                 155                 160

Lys Pro Ala Val Ser His Val Thr His Thr Ile Pro His Ala Asp Tyr
                165                 170                 175

Gly Val Ser Gly Leu Gly Gly Tyr Val Ser Ser Tyr Pro Thr Gly Ala
            180                 185                 190

Ser Ile Asn Thr Val Ser His Gly Ile Ser His Ala Pro Val Tyr Gly
            195                 200                 205

Gly Trp Gly Val Gly Phe Pro Ala Gly Gln Ala Met Ser Thr Val Ala
            210                 215                 220

His Gly Ile His Pro Thr Val Pro Tyr Gly Gly Ile Gly Leu Gly Gly
225                 230                 235                 240

Leu Tyr Gly Gly Tyr Gly Ala His Phe Pro Ala Ala Thr Ser Val Ser
                245                 250                 255

His Thr Thr His Ser Val Pro His Ser Val Gly Trp Gly Leu Gly Gly
                260                 265                 270

Trp Gly Gly Tyr Gly Leu Gly Tyr Gly Val His Ala Pro Val Gly Ala
            275                 280                 285

Ser Val Ser Thr Val Ser His Gly Val His Ala Pro Val Ile His Gly
    290                 295                 300

Gly Ala Thr Leu Ser Thr Val Ser His Gly Val Pro Ala Leu Gly Ala
305                 310                 315                 320

Tyr Gly Gly Tyr Gly Phe Gly Gly Ile Val Gly Gly His Ser Val Tyr
                325                 330                 335

His Pro Thr Gly Thr Ser Val Ser Thr Val Ser His Gly Val Pro Ala
            340                 345                 350

Leu Gly Gly Tyr Gly Glu Tyr Gly Leu Gly Gly Ile Val Gly Gly His
                355                 360                 365

Ser Val Ser Thr Val Ser His Gly Ala Pro Ala Leu Gly Ala Tyr Gly
    370                 375                 380

Gly Tyr Gly Leu Gly Gly Leu Val Gly Gly Phe Gly Ala Tyr His Pro
385                 390                 395                 400

Ala Gly Ser Ser Ile Ser Thr Val Ser His Gly Val His Ala Pro Val
                405                 410                 415

Gly Phe Gly Gly Tyr Gly Leu Gly Tyr Gly Leu Gly Gly Tyr Gly
                420                 425                 430

Leu Gly Gly Tyr Gly Leu Gly Gly Tyr Gly Leu Gly Gly Val Val Gly
                435                 440                 445

Gly Phe Gly Gly Tyr His Pro Val Gly Ser Ser Val Ser Thr Val Ser
```

```
                450             455            460
His Gly Ala Phe Gly Gly His Gly Leu Leu Gly Gly Tyr Gly Val Pro
465                 470             475                 480
Leu Pro Leu Ser Thr Thr Ser His His Thr Val Thr His
                    485             490
```

<210> SEQ ID NO 3
<211> LENGTH: 1680
<212> TYPE: DNA
<213> ORGANISM: Loligo Vulgaris

<400> SEQUENCE: 3

```
atgggagcca tgcaactagc cgtggcctta atcgtacttg aatcagcag ttctgcaaat      60
ggaattttca atggctccac ggccggactt gggagtcagc cttcccctta tcggaaga     120
tctgtcagca ctgtttcaca tggttcccat accctgcgt acggtgggtg gggctacaat    180
cttggtagtt gggggcatgg cctaggtggt ttaggaagtt atggtcttca ctaccccatg    240
tcttcatcag tcagtcatgt ttctcacaca gctcactccc cgctcggata ctatggatgg    300
ggaggttacg gtcaacaatc ccccttaca catgtgtcaa gaaccgctct tcctccagtg    360
ggatgggctt tcggtggact ttacagaggc atggggcac aagtatccca gtctccggtt     420
cgctaccatg gatatagttt tggacgtcca gcagttgcaa cacgccgagt tctctatcca    480
aagccagttg ttagccatgt tactcataca attccccata gcggttgggg catgggtgga    540
tttggtggat atgtttcatc ctatccaact ggtgcttccg ttaacactgt gtctcatgga    600
atcagccatg cccctgttta tggcggctgg ggtgctggtc atgcaataag cactgttgcc    660
catggtattc atcccacagt aacttatgga ggtatgggtc ttggaggtct ctatggagga    720
tatgcgcac actaccctgc atcaacatct gttagccaca ccacacacag tgtacctcat    780
actgtcggtt tgggtcttgg aagcctgcat ggaggatggg gtggttatgg aattggatat    840
gccgtacact ccccagttgg agcttccgta agtaccgtgt ctcatggaat cggtcaccca    900
gtgggttatg gtacatgggg tctcggctct ggtgcacact accctgtcgg tcaatctgta    960
agcactgtgt cacatggcgt tcacgcccct gtagttcatg gaggattggg actttctgga  1020
tcttcagtta gtactgtgtc ccatggagtt ccctccctag gagcatatgg aggatatggc  1080
cttggaggtc ttatcggagg acatagtgtc tatcacccaa ctggatcttc atcagtact   1140
gtgtcccatg gagttccctc ctaggagca tatggaggat atggccttgg aggtcttatc   1200
ggaggacata gtgtctatca cccaactgga tcttccatca gtactgtgtc ccatggagtt  1260
ccctccctag gagcatatgg aggatatggc cttggaggtc ttatcggagg acatagtgtc  1320
tatcacccaa ctggatcttc atcagtact gtgtcccatg gagttccctc ccttggagca   1380
tatgcaggat atggtttggg aggtattgtc ggaggatatg gtgcctataa cccaactggt  1440
tcatctatca gtactgtttc tcatggagtc cactccccag taggttatgg aggatatggt  1500
cttggaggtc ttatcggagg atatggtgcc taccatcccg ctggatcttc atcagtaca   1560
gtgtcacatg gaatcaactc cctaggagca tatggaggat atggcaacgg aggtcttctc  1620
ggaggatatg gtgtcccatt gcctctcagt actacatctc atcatacagt aacacactga  1680
```

<210> SEQ ID NO 4
<211> LENGTH: 27
<212> TYPE: DNA
<213> ORGANISM: artificial sequence
<220> FEATURE:
<223> OTHER INFORMATION: primer

```
<400> SEQUENCE: 4
gccatttgat taagacattt ggtcaat                                      27

<210> SEQ ID NO 5
<211> LENGTH: 30
<212> TYPE: DNA
<213> ORGANISM: artificial sequence
<220> FEATURE:
<223> OTHER INFORMATION: primer

<400> SEQUENCE: 5
ccaccgaaag cccatcccac tggaggaaga                                   30

<210> SEQ ID NO 6
<211> LENGTH: 25
<212> TYPE: DNA
<213> ORGANISM: artificial sequence
<220> FEATURE:
<223> OTHER INFORMATION: primer

<400> SEQUENCE: 6
tcatgatggg agccatgcaa ctagc                                        25

<210> SEQ ID NO 7
<211> LENGTH: 32
<212> TYPE: DNA
<213> ORGANISM: artificial sequence
<220> FEATURE:
<223> OTHER INFORMATION: primer

<400> SEQUENCE: 7
ctcgagccca atcctcagtg tgttactgta tg                                32
```